United States Patent
Gaucher et al.

(10) Patent No.: US 9,511,138 B2
(45) Date of Patent: *Dec. 6, 2016

(54) PHARMACEUTICAL COMPOSITIONS COMPRISING AN ANTIBODY WHICH BINDS THE HUMAN ANTI-MULLERIAN HORMONE RECEPTOR TYPE II

(71) Applicants: LFB BIOTECHNOLOGIES, Les Ulis (FR); CENTRE NATIONAL DE LUTTE CONTRE LE CANCER, Montpellier (FR); I.N.S.E.R.M. (INSTITUT NATIONAL DE LA SANTÉ ET DE LA RECHERCHE MÉDICALE, Paris (FR); UNIVERSITE MONTPELLIER 1, Montpellier (FR)

(72) Inventors: Christine Gaucher, Equedin (FR); Isabelle Navarro-Teulon, Saint Gely du Fesc (FR)

(73) Assignees: LABORATOIRE FRANCAIS DU FRACTIONNEMENT ET DES BIOTECHNOLOGIES, Les Ulis (FR); CENTRE REGIONAL DE LUTTE CONTRE LE CANCER, Montpellier (FR); I.N.S.E.R.M. (INSTITUT NATIONAL DE LA SANTE ET DE LA RECHERCHE MEDICALE), Paris (FR); UNIVERSITE MONTPELLIER 1, Montpellier (FR)

( * ) Notice: Subject to any disclaimer, the term of this patent is extended or adjusted under 35 U.S.C. 154(b) by 5 days.

This patent is subject to a terminal disclaimer.

(21) Appl. No.: 14/367,969

(22) PCT Filed: Dec. 21, 2012

(86) PCT No.: PCT/FR2012/053067
§ 371 (c)(1),
(2) Date: Jun. 23, 2014

(87) PCT Pub. No.: WO2013/093379
PCT Pub. Date: Jun. 27, 2013

(65) Prior Publication Data
US 2015/0004156 A1    Jan. 1, 2015

(30) Foreign Application Priority Data
Dec. 23, 2011  (FR) ...................................... 11 62424

(51) Int. Cl.
| A61K 39/395 | (2006.01) |
| A61K 31/337 | (2006.01) |
| A61K 31/282 | (2006.01) |
| C07K 16/28 | (2006.01) |
| A61K 45/06 | (2006.01) |
| A61K 33/24 | (2006.01) |

(52) U.S. Cl.
CPC ....... *A61K 39/39558* (2013.01); *A61K 31/282* (2013.01); *A61K 31/337* (2013.01); *A61K 33/24* (2013.01); *A61K 39/3955* (2013.01); *A61K 39/39533* (2013.01); *A61K 45/06* (2013.01); *C07K 16/28* (2013.01); *C07K 16/2869* (2013.01)

(58) Field of Classification Search
CPC .................. A61K 39/39558; A61K 39/3955; A61K 31/282; A61K 39/39533; A61K 31/337; C07K 16/2869; C07K 16/28
See application file for complete search history.

(56) References Cited

U.S. PATENT DOCUMENTS

| 4,816,567 A | 3/1989 | Cabilly et al. |
| 5,202,238 A | 4/1993 | Fell et al. |
| 5,204,244 A | 4/1993 | Fell et al. |
| 5,225,539 A | 7/1993 | Winter |
| 5,585,089 A | 12/1996 | Queen et al. |
| 5,639,641 A | 6/1997 | Pedersen et al. |
| 5,766,886 A | 6/1998 | Studnicka et al. |
| 5,770,196 A | 6/1998 | Studnicka |
| 5,821,123 A | 10/1998 | Studnicka |
| 5,869,619 A | 2/1999 | Studnicka |
| 6,331,415 B1 | 12/2001 | Cabilly et al. |
| 6,808,901 B1 | 10/2004 | Neuberger et al. |
| 2004/0005630 A1 | 1/2004 | Studnicka |
| 2005/0239141 A1 | 10/2005 | Studnicka |
| 2006/0188440 A1 * | 8/2006 | Adams ................ A61K 51/103 424/1.49 |

FOREIGN PATENT DOCUMENTS

| EP | 125023 | 11/1984 |
| EP | 0571613 | 12/1993 |
| EP | 0682040 | 11/1995 |
| EP | 1 918 304 | 5/2008 |
| FR | 2 641 468 | 7/1990 |
| WO | 2006/082406 | 8/2006 |
| WO | 2008/053330 | 5/2008 |
| WO | 2011/141653 | 11/2011 |

OTHER PUBLICATIONS

Bakkum-Gamez et al., Gynecol Oncol. Jan. 2008;108(1):141-148.*

(Continued)

*Primary Examiner* — Daniel C Gamett
(74) *Attorney, Agent, or Firm* — Young & Thompson

(57) ABSTRACT

The invention relates to novel pharmaceutical compositions including, as active ingredient, an antibody binding the human anti-Müllerian hormone type II receptor (AMHR-II) and an anticancer agent, as well as the therapeutic applications of these compositions.

24 Claims, 4 Drawing Sheets

(56) References Cited

OTHER PUBLICATIONS

Figure 1:
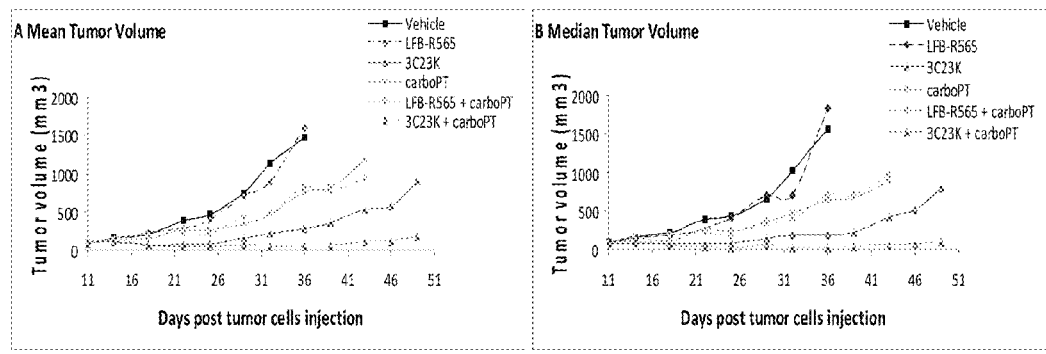

International Search Report dated Apr. 4, 2013, corresponding to PCT/FR2012/053067.
Armstrong, et al.; "Intraperitoneal Cisplatin and Paclitaxel in Ovarian Cancer"; vol. 354, No. 1; Jan. 2006; pp. 34-43.
Penson, et al.; "Phase II Study of Carboplatin, Paclitaxel, and Bevacizumab with Maintenance Bevacizumab as first-line Chemotherapy for Advanced Mu'llerian Tumors"; vol. 28, No. 1, Jan. 1, 2010; pp. 154-159.
Kerri S. Bevis, et al.; "Anti-Tumor Activity of an Anti-DR5 Monoclonal Antibody, TRA-8, in combination with Taxane/Platinum-based chemotherapy in an Ovarian Cancer Model"; vol. 121, No. 1; Jan. 5, 2011; pp. 193-199.

* cited by examiner

```
SEQUENCE LISTING

<160> NUMBER OF SEQ ID NOS: 14

<210> SEQ ID NO 1
<211> LENGTH: 106
<212> TYPE: PRT
<213> ORGANISM: Artificial Sequence
<220> FEATURE:
<223> OTHER INFORMATION: Humanized 12G4 antibody, light chain, variable
      region, without leader
<220> FEATURE:
<221> NAME/KEY: PEPTIDE
<222> LOCATION: (1)..(106)

<400> SEQUENCE: 1

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Ile Tyr
        35                  40                  45

Ser Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 2
<211> LENGTH: 128
<212> TYPE: PRT
<213> ORGANISM: Artificial Sequence
<220> FEATURE:
<223> OTHER INFORMATION: Humanized 12G4 antibody, light chain, variable
      region, with leader
<220> FEATURE:
<221> NAME/KEY: PEPTIDE
<222> LOCATION: (1)..(128)

<400> SEQUENCE: 2

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30
```

Leu Ser Ala Ser Val Gly Asp Arg Val Thr Ile Thr Cys Arg Ala Ser
            35                  40                  45

Ser Ser Val Arg Tyr Ile Ala Trp Tyr Gln Gln Lys Pro Gly Lys Ala
        50                  55                  60

Pro Lys Leu Leu Ile Tyr Ser Thr Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

<210> SEQ ID NO 3
<211> LENGTH: 107
<212> TYPE: PRT
<213> ORGANISM: Artificial Sequence
<220> FEATURE:
<223> OTHER INFORMATION: Humanized 12G4 antibody, light chain, constant
      region

<400> SEQUENCE: 3

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 4
<211> LENGTH: 115
<212> TYPE: PRT
<213> ORGANISM: Artificial Sequence
<220> FEATURE:
<223> OTHER INFORMATION: Humanized 12G4 antibody, heavy chain, variable
      region, without leader
<220> FEATURE:
<221> NAME/KEY: PEPTIDE
<222> LOCATION: (1)..(115)

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

```
Met Glu Leu Ser Ser Leu Arg Ser Glu Asp Thr Ala Val Tyr Tyr Cys
             85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 5
<211> LENGTH: 134
<212> TYPE: PRT
<213> ORGANISM: Artificial Sequence
<220> FEATURE:
<223> OTHER INFORMATION: Humanized 12G4 antibody, heavy chain, variable
      region, with leader
<220> FEATURE:
<221> NAME/KEY: PEPTIDE
<222> LOCATION: (1)..(134)

<400> SEQUENCE: 5

Met Asp Trp Thr Trp Arg Ile Leu Phe Leu Val Ala Ala Thr Gly
1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr His Ile His Trp Val Arg Gln Ala Pro Gly Gln Arg Leu
     50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                 85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

<210> SEQ ID NO 6
<211> LENGTH: 330
<212> TYPE: PRT
<213> ORGANISM: Artificial Sequence
<220> FEATURE:
<223> OTHER INFORMATION: Humanized 12G4 antibody, heavy chain, constant
      region
<220> FEATURE:
<221> NAME/KEY: PEPTIDE
<222> LOCATION: (1)..(330)

<400> SEQUENCE: 6

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 106
<212> TYPE: PRT
<213> ORGANISM: Artificial Sequence
<220> FEATURE:
<223> OTHER INFORMATION: 3C23K antibody, light chain, variable region,
      without leader
<220> FEATURE:
<221> NAME/KEY: PEPTIDE
<222> LOCATION: (1)..(106)

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
```

```
                        85                  90                  95
Phe Gly Gly Gly Thr Lys Val Glu Ile Lys
                100                 105

<210> SEQ ID NO 8
<211> LENGTH: 128
<212> TYPE: PRT
<213> ORGANISM: Artificial Sequence
<220> FEATURE:
<223> OTHER INFORMATION: 3C23K antibody, light chain, variable region,
      with leader
<220> FEATURE:
<221> NAME/KEY: PEPTIDE
<222> LOCATION: (1)..(128)

<400> SEQUENCE: 8

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Thr Tyr Pro Thr Ser Ser Leu Lys Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

<210> SEQ ID NO 9
<211> LENGTH: 115
<212> TYPE: PRT
<213> ORGANISM: Artificial Sequence
<220> FEATURE:
<223> OTHER INFORMATION: 3C23K antibody, heavy chain, variable region,
      without leader
<220> FEATURE:
<221> NAME/KEY: PEPTIDE
<222> LOCATION: (1)..(115)

<400> SEQUENCE: 9

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
```

-continued

```
<210> SEQ ID NO 10
<211> LENGTH: 134
<212> TYPE: PRT
<213> ORGANISM: Artificial Sequence
<220> FEATURE:
<223> OTHER INFORMATION: 3C23K antibody, heavy chain, variable region,
      with leader
<220> FEATURE:
<221> NAME/KEY: PEPTIDE
<222> LOCATION: (1)..(134)

<400> SEQUENCE: 10

Met Asp Trp Thr Trp Arg Ile Leu Phe Leu Val Ala Ala Thr Gly
1               5                   10                  15

Ala His Ser Gln Val Arg Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr His Ile His Trp Val Arg Gln Ala Pro Gly Gln Arg Leu
        50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

<210> SEQ ID NO 11
<211> LENGTH: 213
<212> TYPE: PRT
<213> ORGANISM: Artificial Sequence
<220> FEATURE:
<223> OTHER INFORMATION: 3C23K antibody, light chain, without leader
<220> FEATURE:
<221> NAME/KEY: PEPTIDE
<222> LOCATION: (1)..(213)

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
                20                  25                  30

Ala Trp Tyr Gln Gln Lys Pro Gly Lys Ala Pro Lys Leu Leu Thr Tyr
            35                  40                  45

Pro Thr Ser Ser Leu Lys Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 12
<211> LENGTH: 235
<212> TYPE: PRT
<213> ORGANISM: Artificial Sequence
<220> FEATURE:
<223> OTHER INFORMATION: 3C23K antibody, light chain, with leader
<220> FEATURE:
<221> NAME/KEY: PEPTIDE
<222> LOCATION: (1)..(235)

<400> SEQUENCE: 12

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Thr Tyr Pro Thr Ser Ser Leu Lys Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 13
```

<211> LENGTH: 445
<212> TYPE: PRT
<213> ORGANISM: Artificial Sequence
<220> FEATURE:
<223> OTHER INFORMATION: 3C23K antibody, heavy chain, without leader
<220> FEATURE:
<221> NAME/KEY: PEPTIDE
<222> LOCATION: (1)..(445)

<400> SEQUENCE: 13

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

```
Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 14
<211> LENGTH: 464
<212> TYPE: PRT
<213> ORGANISM: Artificial Sequence
<220> FEATURE:
<223> OTHER INFORMATION: 3C23K antibody, heavy chain, with leader
<220> FEATURE:
<221> NAME/KEY: PEPTIDE
<222> LOCATION: (1)..(464)

<400> SEQUENCE: 14

Met Asp Trp Thr Trp Arg Ile Leu Phe Leu Val Ala Ala Ala Thr Gly
1               5                   10                  15

Ala His Ser Gln Val Arg Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Leu
    50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270
```

```
Thr Pro Glu Val Thr Cys Val Val Asp Val Ser His Glu Asp Pro
        275             280             285
Glu Val Lys Phe Asn Trp Tyr Val Asp Gly Val Glu Val His Asn Ala
        290             295             300
Lys Thr Lys Pro Arg Glu Glu Gln Tyr Asn Ser Thr Tyr Arg Val Val
305             310             315             320
Ser Val Leu Thr Val Leu His Gln Asp Trp Leu Asn Gly Lys Glu Tyr
            325             330             335
Lys Cys Lys Val Ser Asn Lys Ala Leu Pro Ala Pro Ile Glu Lys Thr
            340             345             350
Ile Ser Lys Ala Lys Gly Gln Pro Arg Glu Pro Gln Val Tyr Thr Leu
        355             360             365
Pro Pro Ser Arg Asp Glu Leu Thr Lys Asn Gln Val Ser Leu Thr Cys
        370             375             380
Leu Val Lys Gly Phe Tyr Pro Ser Asp Ile Ala Val Glu Trp Glu Ser
385             390             395             400
Asn Gly Gln Pro Glu Asn Asn Tyr Lys Thr Thr Pro Pro Val Leu Asp
                405             410             415
Ser Asp Gly Ser Phe Phe Leu Tyr Ser Lys Leu Thr Val Asp Lys Ser
            420             425             430
Arg Trp Gln Gln Gly Asn Val Phe Ser Cys Ser Val Met His Glu Ala
            435             440             445
Leu His Asn His Tyr Thr Gln Lys Ser Leu Ser Leu Ser Pro Gly Lys
        450             455             460
```

PHARMACEUTICAL COMPOSITIONS COMPRISING AN ANTIBODY WHICH BINDS THE HUMAN ANTI-MULLERIAN HORMONE RECEPTOR TYPE II

The present invention relates to novel pharmaceutical compositions comprising, as active ingredient, an antibody binding the human anti-Müllerian hormone type II receptor (AMHR-II), as well as the therapeutic uses of these compositions.

The human anti-Müllerian hormone is a glycoprotein of 560 amino acids, a member of the TGF-β family. It is a hormone secreted by the Sertoli cells of the fetal testis, which causes degeneration of the Müllerian duct. It is expressed in the adult in the Sertoli cells and Leydig cells (testis) and the granulosa cells (ovary). It plays a role in the activity of the adult ovary in the regulation of folliculogenesis.

The anti-Müllerian hormone type II receptor (AMHR-II) is a peptide of 573 amino acids and possesses serine-threonine kinase activity. It is involved in the regression of the Müllerian duct associated with the development of the human reproductive system. The Müllerian duct atrophies in men, where it only forms the prostatic vesicle and the sessile hydatid, but persists in women, where it gives rise to the Fallopian tubes, uterus and the greater part of the vagina. This receptor is frequently expressed on human ovarian epithelial tumour cells.

International application WO 2008/053330 describes a murine 12G4 monoclonal antibody directed against AMHR-II for treating ovarian cancers.

International application WO 2011/141653 describes mutated humanized 12G4 antibodies, or fragments thereof, possessing an affinity at least equal to that of the corresponding unmutated chimeric antibody, specificity with respect to the AMHR-II receptor, and not eliciting an immune reaction.

The purpose of the present invention is to propose a therapeutic alternative that is advantageous for patients with a pathology connected with the human anti-Müllerian hormone type II receptor (AMHR-II).

A pathology associated with the human anti-Müllerian hormone type II receptor (AMHR-II) may in particular be: ovarian cancer, in particular metastatic ovarian cancer, serous cancer, hypernephroma, endometrioid, colloidal epithelium, it may also be: prostate cancer, germ cell cancer, endometrial cancer, mixed Müllerian malignant tumour of the uterus, leiomyosarcoma, and endometrial stromal sarcoma.

Ovarian cancer is the main cause of gynaecological cancers and is the fifth commonest cause of mortality from cancer in woman. It has the following three histological origins:
- the surface epithelium (epithelial tumour with various subtypes), which represents 85-90% of ovarian cancers,
- sexual cords/stroma (granulosa tumour (3% of total ovarian cancers)), which represent about 10% of ovarian tumours,
- germ cells, which represent 5% of ovarian cancers.

It is generally asymptomatic during the initial stages, hence its nickname "silent killer" (La Marca A., Volpe A. The Anti-Mullerian hormone and ovarian cancer. Human Reproduction Update, Vol. 13, No. 3 pp. 265-273, 2007).

There are four stages and prognoses (FIGO classification: International Federation of Gynaecology and Obstetrics) for which the survival rate decreases considerably from stage 2:

Stage I: Tumour limited to the ovaries (5-year survival: 90-70%),
Stage II: Tumour in one or two ovaries and extends to pelvis (5-year survival: 70-40%),
Stage III: Tumour in one or two ovaries, extending outside the pelvis (5-year survival: 20%),
Stage IV: Distant metastases excluding peritoneal metastases (5-year survival: <10%),
(Fauci, Braunwald et al. Principles of internal medicine. Harrison's 17th edition/National Cancer Institute cancer.gov/CNGOF (French National Colleges of Gynaecologists and Obstetricians).

Regarding ovarian cancer, the main strategies used for treatment are surgery and chemotherapy, in particular as first-line treatment, such as a mixture of carboplatin and paclitaxel.

Monoclonal antibodies have also recently been developed such as cetuximab, which is directed against the epidermal growth factor receptor (EGFR, Ozols R. F. et al., Focus on epithelial ovarian cancer, Cancer Cell. 2004, January; 5(1): 19-24). Other monoclonal antibodies are currently in phase III, such as abagovomab directed against CA-125, avastin directed against vascular endothelial growth factor (VEGF-A), or farletuzumab directed against folate receptor alpha (FRA).

The purpose of the present invention is to propose a therapy directed against a target different from the antibody targets currently developed. The invention offers the advantage of proposing a treatment against various pathologies associated with AMHR-II. Moreover, in the case of ovarian cancer, the invention offers the possibility of a therapy that is more effective than the reference therapy for reducing tumour volume, thus allowing a quicker improvement in the patient's condition.

This purpose is achieved by means of a composition according to the invention.

The present invention relates to a pharmaceutical composition comprising, as active ingredient, in combination with a pharmaceutically acceptable vehicle,
an anticancer agent, and
an antibody binding the human anti-Müllerian hormone type II receptor (AMHR-II).

In the invention, the term "antibody" refers to an immunoglobulin, a multimeric protein consisting of 4 chains, i.e. 2 light chains and 2 heavy chains, each comprising a variable region and a constant region. More precisely, each light chain consists of a variable region ($V_L$) and a constant region ($C_L$). Each heavy chain consists of a variable region ($V_H$) and a constant region consisting of three constant domains $C_{H1}$, $C_{H2}$ and $C_{H3}$. The domains $C_{H2}$ and $C_{H3}$ make up the domain Fc. The variable region of the light chain consists of three regions determining recognition of the antigen (complementarity determining region, CDR) surrounded by four framework domains. The three-dimensional folding of the variable region is such that the 3 CDRs are exposed on the same side of the protein and allow formation of a specific structure recognizing a defined antigen.

An "anticancer agent" is defined as any molecule that can either interfere with the biosynthesis of macromolecules (DNA, RNA, proteins, etc.) or inhibit cellular proliferation, or lead to cell death by apoptosis or cytotoxicity for example. Among the anticancer agents, there may be mentioned alkylating agents, topoisomerase inhibitors and intercalating agents, anti-metabolites, cleaving agents, agents interfering with tubulin, monoclonal antibodies.

A "pharmaceutically acceptable vehicle" refers to a non-toxic material that is compatible with a biological system such as a cell, a cell culture, a tissue or an organism.

According to a particular aspect, the invention relates to a pharmaceutical composition comprising, as active ingredient, in combination with a pharmaceutically acceptable vehicle, an anticancer agent and an antibody binding AMHR-II, in which said antibody binding AMHR-II is a polyclonal antibody.

The term "polyclonal antibody" denotes a mixture of antibodies, capable of recognizing various antigenic determinants of a target protein.

According to another particular aspect, the invention relates to a pharmaceutical composition comprising, as active ingredient, in combination with a pharmaceutically acceptable vehicle, an anticancer agent, and an antibody binding AMHR-II, in which said antibody is a monoclonal antibody, and preferably a chimeric or humanized 12G4 monoclonal antibody.

A "monoclonal antibody" is defined as an antibody that only recognizes a single antigenic determinant of the target protein.

By "chimeric monoclonal antibody" is meant an antibody in which the variable regions of the light chains and heavy chains belong to a species different from that of the constant regions of the light chains and heavy chains. By extension or usage a chimeric antibody refers to an antibody with constant portions of human origin.

The chimeric antibodies according to the invention may be prepared using the techniques of genetic recombination. For example, a chimeric antibody may be produced by constructing a chimeric gene comprising a nucleotide sequence of complementary DNA (cDNA) or a genomic sequence with introns coding for the variable region of the heavy chain of a murine monoclonal antibody, joined to a nucleotide sequence coding for the constant region of the heavy chain of a human antibody, and by constructing a chimeric gene comprising a nucleotide sequence coding for the variable region of the light chain of a murine monoclonal antibody, joined to a nucleotide sequence coding for the constant region of the light chain of a human antibody. By transfecting said chimeric genes, by protoplast fusion or any other technique, into a cell line, of murine myeloma for example, production of mouse-human chimeric antibodies by the transformed cells is obtained. It is the document Morrison et al., Proc. Natl. Acad. Sci. U.S.A., 81, pp. 6851-55 (1984) that described the preparation of such antibodies for the first time. The documents Boulianne, G. L. et al., Nature, 312: 643-646 (1984), Sun, L. K., et al., Proc. Natl. Acad. Sci. USA (1984), 214-218, U.S. Pat. Nos. 4,816,567, 6,331,415, 6,808,901 and EP 125023 could also be used as reference by a person skilled in the art, as well as Bobrzecka, K., et al., Immunology Letters 2, pp 151-155, which describes a procedure of splitting of the interchain disulphide bridges of the immunoglobulins followed by ordered rearrangement of these same disulphide bridges in order to obtain antibodies formed from rabbit Fab fragments and human Fc fragments.

Another possible approach for the preparation of chimeric antibodies, as described in document FR 2 641 468, is to graft Fab' fragments of a murine monoclonal antibody onto human polyclonal immunoglobulins, in particular IgG, or onto Fc fragments, using a coupling agent, for example a diimide. Chimeric antibodies of the type Ig-Fab' (also designated Fab'-Ig), Fc-Fab' or (Fab')2 may thus be obtained. Such chimeric antibodies are characterized by grafting the whole of the Fab' fragment, and not only the variable portions.

Alternatively, other authors have described the production of monovalent chimeric antibodies by grafting Fab' fragments of polyclonal antibodies onto IgG or onto Fc fragments (G. T. Stevenson et al., Med. Oncol. & Tumor, 1985, Pharmacother., Vol. 1, No. 4, 275-278, 1984).

Homologous recombination in vivo between the portions of the genes coding for the constant regions of the light chains and heavy chains of a murine immunoglobulin by portions of the genes coding for the constant regions of the light chains and heavy chains of a human immunoglobulin is also a means that may be used in order to obtain such antibodies (U.S. Pat. Nos. 5,204,244 or 5,202,238). This is not an exhaustive list.

By "humanized monoclonal antibody" is meant an antibody in which some or all of the sequences of the regions involved in antigen recognition (the hypervariable regions (CDR: Complementarity Determining Region), and sometimes certain amino acids of the FR regions (Framework regions)), are of non-human origin (preferably murine) whereas the sequences of the constant regions and variable regions not involved in antigen recognition are of human origin.

The humanized antibodies according to the invention may be prepared by well-known techniques, such as that described for the first time in the document by Jones et al., Nature, 1986, 321-522-525. This involved replacing the hypervariable regions (CDRs) of a human antibody with hypervariable regions of murine origin, both at the level of the light chains but also of the heavy chains. This technique, now well known to a person skilled in the art under the name "CDR grafting", is described in numerous documents such as Singer et al., J. Immun. 150: 2844-2857 (1993), Riechman et al., Nature, Vol. 332, 323: 326 (1988), or in U.S. Pat. Nos. 5,225,539; 5,585,089; EP 0682040, which may also be used as reference.

However, most of the humanized antibodies produced by grafting of the CDR regions have reduced affinity relative to a murine antibody, owing to the major role of certain amino acids of the framework regions in the spatial positioning of the non-human amino acids including the CDRs as well as in the binding to the antigen. That is why today a person skilled in the art quite often replaces, in the human receiving Ig, not only the CDRs, but also the residues of the framework regions that may contribute to the binding site of the antigen.

Another technique for humanizing antibodies is the technique of grafting the specific determining residues (Specificity Determining Region, SDR), which consists of no longer grafting the whole of the CDR regions, but only the SDR regions of the non-human antibody in the human variable regions (Tamura et al., J Immunol. 2000; 164: 1432-41). The SDR regions are defined as the regions of the CDRs in direct contact with the antigen (Padlan et al. (1995), FASEB J. 9: 133-139). This technique therefore requires identification of the SDRs. This may be done, for example, by determining the 3D structure of the antigen-antibody complex, using the database of the SDRs already identified (http://paradox.harvard.edu/sdr), or else by comparing the human variable sequences with those of the non-human species, using computer software such as DomainGapAlign, CLUSTALW2, CLUSTALX, BLAST or FASTA.

Another alternative for obtaining humanized antibodies consists of grafting regions called "abbreviated CDRs" ("grafting of abbreviated CDRs"). It involves grafting the SDR regions and some adjacent residues, upstream and downstream of the sequence. The documents by De Pascalis et al., The Journal of Immunology, 2002, 169: 3076-3084; Kashmiri Syed V. S et al., Methods, Volume 36, Issue, May 2005, Pages 25-34 will be able to be used as reference.

The composite humanization technology developed by Antitope (WO 2006082406) is a CDR grafting technique that considers the framework regions independently and aims to select the human equivalents separately in such a way that the presentation of the residues interacting with the antigen are better conserved in their orientation.

The so-called resurfacing technique, "variable domain resurfacing", also called "veneering", as developed by ImmunoGen (U.S. Pat. No. 5,639,641) or Xoma (EP 0571613, U.S. Pat. Nos. 5,766,886, 5,770,196, 5,821,123, 5,869,619) may also be used. This technology consists of giving a human "profile" to a mouse variable domain by replacing the residues exposed on the surface in the framework regions of the murine antibodies with the residues usually found on the surface of the human antibodies. The documents by Roguska et al., Proc Natl Acad Sci USA 1994; Mark G. E. et al. (1994) in Handbook of Experimental Pharmacology Vol. 113: The pharmacology of monoclonal Antibodies, Springer-Verlag, pp 105-134 may also serve as reference.

The Germliner™ platform developed by AvantGen may also be used (http://www.avantgen.com/AvantGensTechnologiesandServices.pdf). This makes it possible to obtain humanized antibodies in which only CDR3s are of non-human origin.

This is not an exhaustive list. Obtaining said humanized antibodies will, moreover, preferably be coupled to an affinity maturation process.

The production of the humanized 12G4 monoclonal antibody is described in detail in international application WO 2011/141653. The antibodies described in the invention are isolated and purified. These antibodies are mature, i.e. they possess an ad hoc three-dimensional structure allowing them to recognize the antigen, and possess all the post-translational modifications essential to their antigenic recognition, in particular glycosylation and the formation of intramolecular and intermolecular disulphide bridges.

According to another aspect, the invention relates to a fragment of a mutated humanized 12G4 monoclonal antibody as defined above, selected from the group of fragments consisting of: Fc, Fab'-SH, Fd, Fv, Fab, F(ab')2, Fab', dsFv, scFv, Sc(Fv)2, diabody, triabody or tetrabody or also nanobody.

According to an even more particular aspect, the invention relates to a pharmaceutical composition comprising, as active ingredient, in combination with a pharmaceutically acceptable vehicle, an anticancer agent, and an antibody binding AMHR-II, in which the chimeric or humanized 12G4 monoclonal antibody is mutated, and comprises at least one mutation in the light and/or heavy chain.

According to an even more particular aspect, the invention relates to a pharmaceutical composition comprising, as active ingredient, in combination with a pharmaceutically acceptable vehicle, an anticancer agent, and an antibody binding AMHR-II, in which the chimeric or humanized 12G4 monoclonal antibody is mutated, comprises at least one mutation in the light and/or heavy chain, and has an affinity for AMHR-II characterized by a $K_D$ preferably less than $10^{-7}$ M, in particular less than $10^{-8}$ M, in particular in the range from $10^{-9}$ M to $10^{-11}$ M.

More particularly, the present invention relates to a pharmaceutical composition comprising, as active ingredient, in combination with a pharmaceutically acceptable vehicle, an anticancer agent, and a monoclonal antibody binding AMHR-II, in which said monoclonal antibody is a humanized 12G4 antibody, or a fragment of humanized 12G4 monoclonal antibody, said humanized 12G4 monoclonal antibody being mutated, and comprises at least one mutation in the light and/or heavy chain, said mutated antibody possessing an affinity for the human anti-Müllerian hormone type II receptor (AMHRII) characterized by a $K_D$ preferably less than $10^{-7}$ M, in particular less than $10^{-8}$ M, in particular in the range from $10^{-9}$ M to $10^{-11}$ M.

By "mutated humanized 12G4 monoclonal antibody" is meant a humanized 12G4 monoclonal antibody in which at least one mutation was carried out in the variable region of the light chain and/or the constant region of the light chain and/or the variable region of the heavy chain or the constant region of the heavy chain. A mutated humanized 12G4 antibody, in a composition according to the invention, has an affinity at least equal to that of the corresponding unmutated chimeric antibody, a specificity with respect to AMHR-II and does not elicit an immune reaction.

Even more particularly, the present invention relates to a pharmaceutical composition comprising, as active ingredient, in combination with a pharmaceutically acceptable vehicle, an anticancer agent, and a monoclonal antibody binding AMHR-II, in which said mutated humanized monoclonal antibody comprises or is constituted by:

a) a light chain comprising or constituted by:
  a variable region the amino acid sequence of which is represented by SEQ ID NO: 1 or SEQ ID NO: 2, and
  a constant region the amino acid sequence of which is represented by SEQ ID NO: 3 or by a sequence having at least 80% homology with SEQ ID NO: 3 b) a heavy chain comprising or constituted by:
  a variable region the amino acid sequence of which is represented by SEQ ID NO: 4, or SEQ ID NO: 5, and
  a constant region the amino acid sequence of which is represented by SEQ ID NO: 6 or by a sequence having at least 80% homology with SEQ ID NO: 6, in which the humanized 12G4 monoclonal antibody comprises at least one mutation in the light and/or heavy chain, and has a $K_D$ for the human anti-Müllerian hormone type II receptor (AMHR-II) preferably less than $10^{-7}$ M, in particular less than $10^{-8}$ M, in particular in the range from $10^{-9}$ M to $10^{-11}$ M. According to an even more particular aspect, the invention relates to a pharmaceutical composition comprising, as active ingredient, in combination with a pharmaceutically acceptable vehicle, an anticancer agent, and an antibody binding AMHR-II, in which the chimeric or humanized 12G4 monoclonal antibody is mutated, and comprises at least one mutation in the light and/or heavy chain. The references of the amino acid sequences of the different portions of the antibodies are presented in the following table:

|  | Sequence references in the present invention | Sequence reference in application WO 2011/141653 |
|---|---|---|
| Humanized 12G4 antibody, light chain, variable region, without leader | SEQ ID NO: 1 | SEQ ID NO: 2 |
| Humanized 12G4 antibody, light chain, variable region, with leader | SEQ ID NO: 2 | SEQ ID NO: 4 |
| Humanized 12G4 antibody, light chain, constant region, | SEQ ID NO: 3 | SEQ ID NO: 6 |

-continued

| | Sequence references in the present invention | Sequence reference in application WO 2011/141653 |
|---|---|---|
| Humanized 12G4 antibody, heavy chain, variable region, without leader | SEQ ID NO: 4 | SEQ ID NO: 8 |
| Humanized 12G4 antibody, heavy chain, variable region, with leader | SEQ ID NO: 5 | SEQ ID NO: 10 |
| Humanized 12G4 antibody, heavy chain, constant region | SEQ ID NO: 6 | SEQ ID NO: 12 |
| 3C23K antibody, light chain, variable region, without leader | SEQ ID NO: 7 | SEQ ID NO: 34 |
| 3C23K antibody, light chain, variable region, with leader | SEQ ID NO: 8 | SEQ ID NO: 36 |
| 3C23K antibody, heavy chain, variable region, without leader | SEQ ID NO: 9 | SEQ ID NO: 38 |
| 3C23K antibody, heavy chain, variable region, with leader | SEQ ID NO: 10 | SEQ ID NO: 40 |
| 3C23K antibody, light chain, without leader | SEQ ID NO: 11 | SEQ ID NO: 82 |
| 3C23K antibody, light chain, with leader | SEQ ID NO: 12 | SEQ ID NO: 84 |
| 3C23K antibody, heavy chain, without leader | SEQ ID NO: 13 | SEQ ID NO: 86 |
| 3C23K antibody, heavy chain, with leader | SEQ ID NO: 14 | SEQ ID NO: 88 |

Even more particularly, the present invention relates to a pharmaceutical composition comprising, as active ingredient, in combination with a pharmaceutically acceptable vehicle, an anticancer agent, and a monoclonal antibody binding AMHR-II, in which said mutated humanized monoclonal antibody comprises or is constituted by:
a) a light chain comprising or constituted by:
   a variable region the amino acid sequence of which is represented by SEQ ID NO: 7 or SEQ ID NO: 8,
   a constant region the amino acid sequence of which is represented by SEQ ID NO: 3
b) a heavy chain comprising or constituted by:
   a variable region the amino acid sequence of which is represented by SEQ ID NO: 9 or SEQ ID NO: 10
   a constant region the amino acid sequence of which is represented by SEQ ID NO: 6

Even more particularly, the present invention relates to a pharmaceutical composition comprising, as active ingredient, in combination with a pharmaceutically acceptable vehicle, an anticancer agent, and a monoclonal antibody binding AMHR-II, in which said mutated humanized monoclonal antibody comprises or is constituted by:
a) a light chain constituted by the amino acid sequence represented by SEQ ID NO: 11 (without leader) or SEQ ID NO: 12 (with leader), and
b) a heavy chain comprising or constituted by the amino acid sequence represented by SEQ ID NO: 13 (without leader), or SEQ ID NO: 14 (with leader).

Even more particularly, the present invention relates to a pharmaceutical composition comprising, as active ingredient, in combination with a pharmaceutically acceptable vehicle, an anticancer agent, and a monoclonal antibody binding AMHR-II, in which said mutated humanized monoclonal antibody is produced by the 3C23K clone.

The mutated humanized monoclonal antibody produced by the 3C23K clone is described in detail in international application WO 2011/141653. By reference to the humanized 12G4 monoclonal antibody, the 3C23K antibody has the mutations of the 3C_23 antibody, as well as an additional mutation, in the CDR of the variable region of the light chain (E184K) in which a glutamic acid is replaced with a lysine, i.e. replacement of an acidic amino acid with a basic amino acid consequently having a totally different charge since it is of opposite sign, yet still displays an activity but especially an affinity far better than that of the unmutated humanized 12G4 antibody, and greater than that of the unmutated chimeric 12G4 antibody, and does not cause an immune reaction.

The mutated humanized monoclonal antibody produced by the 3C23K clone displays fucosylation with a content of about 50%.

According to another aspect, the present invention relates to a pharmaceutical composition comprising, as active ingredient, in combination with a pharmaceutically acceptable vehicle, an anticancer agent, and a monoclonal antibody binding AMHR-II, in which said mutated humanized monoclonal antibody is produced by a clone described in application WO 2011/141653 and selected from the group consisting of: 3C_23, 6B_78, 4C_35 and 5B_42.

In a particular embodiment, the invention relates to a pharmaceutical composition comprising, as active ingredient, in combination with a pharmaceutically acceptable vehicle, an anticancer agent, and an antibody binding AMHR-II, in which said antibody is a recombinant antibody produced by animal transgenesis.

This recombinant antibody may thus be produced by any technique known to a person skilled in the art, for example by recombination in a host cell, transformed with one or more vector(s) that allow the expression and/or the secretion of the nucleotide sequences coding for the heavy chain and/or the light chain of the antibody. The vector generally comprises a promoter, translation start and stop signals, as well as appropriate regions for the regulation of transcription. It is maintained stably in the host cell and may optionally possess particular signals that specify the secretion of the translated protein. These different elements are selected and optimized by a person skilled in the art in relation to the cellular host used. Such vectors are prepared by methods commonly used by a person skilled in the art, and the resultant clones may be introduced into a suitable host by standard methods. The cellular host may be selected from prokaryotic or eukaryotic systems, for example bacterial cells but also yeast cells or animal cells, especially mammalian cells. The mammalian cells preferred for the production of the monoclonal antibodies are the YB2/0 rat line, the CHO hamster line, PER.C6™ (Crucell), 293, K562, NSO, SP2/0, BHK or COS. It is also possible to use insect cells. Another method of production is the expression of the recombinant antibody in transgenic organisms, for example in plants or especially in the milk of transgenic animals such as the rabbit, goat or pig. According to a preferred embodiment, the antibody is produced in the milk of non-human transgenic mammals, genetically modified to produce this glycoprotein. Preferably, it is milk of a transgenic rabbit or goat, preferably in the milk of a transgenic goat. Advantageously, the antibody produced by animal transgenesis, in particular in the mammary glands of a transgenic goat, has a glycosylation with a high degree of galactosylation, for example greater than 70%.

In particular, the invention relates to a pharmaceutical composition comprising, as active ingredient, in combination with a pharmaceutically acceptable vehicle, an anticancer agent, and an antibody binding AMHR-II, in which the anticancer agent is paclitaxel or a platinum salt selected from the group consisting of: oxaliplatin, cisplatin and carboplatin.

The anticancer agent may also be selected from chemotherapeutic agents other than the platinum salts, small molecules, monoclonal antibodies or else anti-angiogenesis peptibodies.

The chemotherapeutic agents other than the platinum salts include the intercalating agents (blocking of DNA replication and transcription), such as the anthracyclines (doxorubicin, pegylated liposomal doxorubicin), the topoisomerase inhibitors (camptothecin and derivatives: Karenitecin, topotecan, irinotecan), or else SJG-136, the inhibitors of histone deacetylase (vorinostat, belinostat, valproic acid), the alkylating agents (bendamustine, glufosfamide, temozolomide), the anti-mitotic plant alkaloids, such as the taxanes (docetaxel, paclitaxel), the vinca alkaloids (vinorelbine), the epothilones (ZK-Epothilone, ixabepilone), the anti-metabolites (gemcitabine, elacytarabine, capecitabine), the kinesin spindle protein (KSP) inhibitors (ispinesib), trabectedin or else ombrabulin (combretastatin A-4 derivative).

Among the small molecules there are the poly(ADP-ribose)polymerase (PARP) inhibitors: olaparib, iniparib, veliparib, rucaparib, CEP-9722, MK-4827, BMN-673, the kinase inhibitors, such as the tyrosine kinase inhibitors (TKI) among which there may be mentioned the anti-VEGFR molecules (sorafenib, sunitinib, cediranib, vandetanib, pazopanib, BIBF 1120, semaxanib, Cabozantinib, motesanib), the anti-HER2/EGFR molecules (erlotinib, gefitinib, lapatinib), the anti-PDGFR molecules (imatinib, BIBF 1120), the anti-FGFR molecules (BIBF 1120), the aurora kinase/tyrosine kinase inhibitors (ENMD-2076), the Src/Abl kinase inhibitor (Saracatinib), or also Perifosine, Temsirolimus (mTOR inhibitor), alvocidib (cyclin-dependent kinase inhibitor), Volasertib (inhibitor of PLK1 (polo-like kinase 1) protein, LY2606368 (inhibitor of checkpoint kinase 1 (chk 1), GDC-0449 (Hedgehog Pathway Inhibitor), Zibotentan (antagonist of the ETA-receptor), Bortezomib, Carfilzomib (proteasome inhibitor), cytokines such as IL-12, IL-18, IL-21, INF-alpha, INF-gamma.

Among the antibodies, there may be mentioned, the anti-VEGF: bevacizumab, the anti-VEGFR: ramucirumab, the anti-HER2/EGFRs: trastuzumab, pertuzumab, cetuximab, panitumumab, MGAH22, matuzumab, anti-PDGFR alpha: IMC-3G3, the anti-folate receptor: farletuzumab, the anti-CD27: CDX-1127, the anti-CD56: BB-10901, the anti-CD105: TRC105, the anti-CD276: MGA271, the anti-AGS-8: AGS-8M4, the anti-DR5: TRA-8, the anti-HB-EGF: KHK2866, the anti-mesothelins: amatuximab, BAY 94-9343 (immunotoxin), catumaxomab (EpCAM/CD3 bispecific antibody), the anti-IL2R: daclizumab, the anti-IGF-1R: ganitumab, the anti-CTLA-4: ipilimumab, the anti-Lewis Y: Hu3S193, SGN-15 (immunotoxin), the anti-CA125: oregovomab, the anti-HGF: rilotumumab, the anti-IL6: siltuximab, the anti-TR2: tigatuzumab, the anti-alpha5 beta1 integrin: volociximab, the anti-HB-EGF: KHK2866.

The anti-angiogenesis peptibodies are selected from AMG 386 and CVX-241.

More particularly, the invention relates to a pharmaceutical composition comprising, as active ingredient, in combination with a pharmaceutically acceptable vehicle, an anticancer agent, and an antibody binding AMHR-II, in which the anticancer agent is carboplatin.

Even more particularly, the invention relates to a pharmaceutical composition comprising, as active ingredient, in combination with a pharmaceutically acceptable vehicle, an anticancer agent, and an antibody binding AMHR-II, in which the mutated humanized monoclonal antibody is produced by the 3C23K clone and the anticancer agent is carboplatin.

In a particular aspect, the invention relates to a pharmaceutical composition comprising, as active ingredient, in combination with a pharmaceutically acceptable vehicle, an anticancer agent, and an antibody binding AMHR-II, in which the anticancer agent is paclitaxel.

In a more particular aspect, the invention relates to a pharmaceutical composition comprising, as active ingredient, in combination with a pharmaceutically acceptable vehicle, an anticancer agent, and an antibody binding AMHR-II, in which the mutated humanized monoclonal antibody is produced by the 3C23K clone and the anticancer agent is paclitaxel.

In a particular aspect, the present invention relates to a pharmaceutical composition comprising, as active ingredient, in combination with a pharmaceutically acceptable vehicle, an anticancer agent, and an antibody binding AMHR-II, in a formulation intended for administration by the intravenous or intraperitoneal route.

The pharmaceutical composition of the invention may be administered by any suitable administration route, for example by the parenteral, oral, sublingual, vaginal, rectal, or transdermal route, preferably by intravenous, subcutaneous or intradermal injection. Intramuscular, intraperitoneal, intrasynovial, intrathecal or intratumoral injection is also possible. The injections may be carried out in the form of a bolus, or by continuous infusion. When the antibody composition and the composition of anticancer agent are administered separately, these compositions may be in an identical or different form of administration.

The preparations for parenteral administration may include sterile aqueous or non-aqueous solutions, suspensions or emulsions. Examples of non-aqueous solvents are propylene glycol, polyethylene glycol, vegetable oils, such as olive oil, or injectable organic esters such as ethyl oleate. Aqueous vehicles comprise water, alcohol/water solutions, and emulsions or suspensions.

The pharmaceutical compositions according to the invention advantageously comprise one or more pharmaceutically acceptable excipients or vehicles. There may be mentioned for example saline, physiological, isotonic, buffered solutions, etc., compatible with pharmaceutical use and known to a person skilled in the art. The compositions may contain one or more agents or vehicles selected from dispersants, solubilizers, stabilizers, preservatives, etc. Agents or vehicles usable in formulations (liquid and/or injectable and/or solid) are in particular methylcellulose, hydroxymethylcellulose, carboxymethylcellulose, polysorbate 80, mannitol, gelatin, lactose, vegetable oils, acacia, etc. The compositions may be formulated in the form of injectable suspensions, gels, oils, tablets, suppositories, powders, hard gelatine capsules, soft capsules, etc.

According to a particular aspect, the invention relates to a pharmaceutical composition comprising, as active ingredient, in combination with a pharmaceutically acceptable vehicle, an anticancer agent and an antibody binding AMHR-II, in which the therapeutically effective quantity of antibody administered to a patient is in a range from about 0.07 mg to about 35000 mg, preferably from about 0.7 mg to about 7000 mg, preferably from about 0.7 mg to about 1400 mg, preferably from about 0.7 mg to about 700 mg, and more preferably from about 0.7 mg to about 70 mg.

The dosage of the active ingredient depends in particular on the administration method, and is easily determined by a person skilled in the art. A therapeutically effective quantity (unit dose) of antibody may vary from 0.01 mg/kg to 500 mg/kg, preferably from 0.1 mg/kg to 500 mg/kg, preferably from 0.1 mg/kg to 100 mg/kg, preferably from 0.1 mg/kg to 20 mg/kg, preferably from 0.1 mg/kg to 10 mg/kg, and more preferably from 1 mg/kg to 10 mg/kg, in one or more weekly administrations, for several weeks or months. The effective unit dose may therefore easily be deduced from a dose calculated for an "average" patient with a weight of 70 kg.

According to another particular aspect, the invention relates to a pharmaceutical composition comprising, as active ingredient, in combination with a pharmaceutically acceptable vehicle, an anticancer agent and an antibody binding AMHR-II, in which the therapeutically effective quantity of anticancer agent administered to a patient is in a range from about 10 mg to about 700 mg, preferably in a range from about 20 mg to about 350 mg, and preferably is about 110 mg.

The dosage of the anticancer agent depends in particular on the administration method, and is easily determined by a person skilled in the art. A therapeutically effective quantity (unit dose) may vary from 0.2 mg/m$^2$ to 10 g/m$^2$, preferably from 0.2 mg/m$^2$ to 1 g/m$^2$, preferably from 2 mg/m$^2$ to 1 g/m$^2$, preferably from 20 mg/m$^2$ to 1 g/m$^2$, and more preferably from 20 mg/m$^2$ to 0.5 g/m$^2$, in one or more weekly administrations, for several weeks or months. The effective unit dose may therefore be deduced from a dose calculated for an "average" patient whose body surface area is about 1.8 m$^2$.

According to an even more particular aspect, the invention relates to a pharmaceutical composition comprising, as active ingredient, in combination with a pharmaceutically acceptable vehicle, an anticancer agent and an antibody binding AMHR-II, in which the therapeutically effective quantity of anticancer agent administered to a patient is about 110 mg, and the therapeutically effective quantity of antibody administered to the patient is about 70 mg.

The invention also relates to a composition comprising an anticancer agent and an antibody binding the human anti-Müllerian hormone type II receptor (AMHR-II), for use as a medicinal product in the prevention or treatment of a pathology associated with the human anti-Müllerian hormone type II receptor (AMHR-II).

By "treatment" is meant the means for treating a manifest pathology, the symptoms of which are visible. By "prevention" is meant the means for preventing said pathology from occurring.

A pathology associated with the human anti-Müllerian hormone type II receptor (AMHR-II) may in particular be:
  ovarian cancer, in particular metastatic ovarian cancer, and its various subtypes, in particular: serous, clear-cell, endometrioid, mucinous,
  germ cell cancer,
  endometrial cancer,
  mixed Müllerian malignant tumour of the uterus,
  leiomyosarcoma,
  endometrial stromal sarcoma,
  prostate cancer,
  testicular cancer.

Tumours expressing the AMHR-II antigen are targeted preferentially, i.e. tumours in which a significant level of expression of the AMHR-II antigen in a cell is observed, preferably on the surface of the cells.

According to the invention, the two therapeutic agents are used in combination in order to potentiate the antiproliferative effects of both of them.

In a particular aspect, the invention relates to a composition for use as a medicinal product in the prevention or treatment of a pathology associated with AMHR-II, comprising an anticancer agent and an antibody binding AMHR-II, in which said antibody is a polyclonal antibody.

According to another particular aspect, the invention relates to a composition for use as a medicinal product in the prevention or treatment of a pathology associated with AMHR-II, comprising an anticancer agent and an antibody binding AMHR-II, in which said antibody is a monoclonal antibody, and preferably a chimeric or humanized 12G4 monoclonal antibody.

According to another particular aspect, the invention relates to a composition for use as a medicinal product in the prevention or treatment of a pathology associated with AMHR-II, comprising an anticancer agent and an antibody binding AMHR-II, in which said antibody is a mutated humanized 12G4 antibody, or a fragment of mutated humanized 12G4 monoclonal antibody, in which said monoclonal antibody comprises at least one mutation in the light and/or heavy chain.

According to another particular aspect, the invention relates to a composition for use as a medicinal product in the prevention or treatment of a pathology associated with AMHR-II, comprising an anticancer agent and an antibody binding AMHR-II, in which said antibody is a mutated humanized 12G4 antibody, or a fragment of mutated humanized 12G4 monoclonal antibody, in which said monoclonal antibody comprises at least one mutation in the light and/or heavy chain and has an AMHR-II affinity characterized by a $K_D$ preferably less than $10^{-7}$ M, in particular less than $10^{-8}$ M, in particular in the range from $10^{-9}$ M to $10^{-11}$ M. According to another particular aspect, the invention relates to a composition for use as a medicinal product in the prevention or treatment of a pathology associated with AMHR-II, comprising an anticancer agent and an antibody binding AMHR-II, in which said antibody is a mutated humanized 12G4 antibody, or a fragment of mutated humanized 12G4 monoclonal antibody, in which said monoclonal antibody comprises at least one mutation in the light and/or heavy chain.

According to another particular aspect, the invention relates to a composition for use as a medicinal product in the prevention or treatment of a pathology associated with AMHR-II, comprising an anticancer agent and an antibody binding AMHR-II, in which said 12G4 antibody comprises or is constituted by:
  a) a light chain comprising or constituted by:
    a variable region the amino acid sequence of which is represented by SEQ ID NO: 1 or SEQ ID NO: 2, and
    a constant region the amino acid sequence of which is represented by SEQ ID NO: 3 or having at least 80% homology with SEQ ID NO: 3,
  b) a heavy chain comprising or constituted by:
    a variable region the amino acid sequence of which is represented by SEQ ID NO: 4, or SEQ ID NO: 5, and
    a constant region the amino acid sequence of which is represented by SEQ ID NO: 6 or by a sequence having at least 80% homology with SEQ ID NO: 6,
in which the humanized 12G4 monoclonal antibody is mutated, comprises at least one mutation in the light and/or heavy chain, and has a $K_D$ for the human anti-Müllerian hormone type II receptor (AMHR-II) preferably less than $10^{-7}$ M, in particular less than $10^{-8}$ M, in particular in the range from $10^{-9}$ M to $10^{-11}$ M.

In a particular aspect, the invention relates to a composition for use as a medicinal product in the prevention or treatment of a pathology associated with AMHR-II, comprising an anticancer agent and an antibody binding AMHR-II, in which the humanized monoclonal antibody comprises or is constituted by a) a light chain comprising or constituted by:
   a variable region the amino acid sequence of which is represented by SEQ ID NO: 7 or SEQ ID NO: 8,
   a constant region the amino acid sequence of which is represented by SEQ ID NO: 3
b) a heavy chain comprising or constituted by:
   a variable region the amino acid sequence of which is represented by SEQ ID NO: 9 or SEQ ID NO: 10, and
   a constant region the amino acid sequence of which is represented by SEQ ID NO: 6.

In a particular aspect, the invention relates to a composition for use as a medicinal product in the prevention or treatment of a pathology associated with AMHR-II, comprising an anticancer agent and an antibody binding AMHR-II, in which the humanized 12G4 monoclonal antibody is produced by the clone 3C-23K.

In a particular aspect, the invention relates to a composition for use as a medicinal product in the prevention or treatment of a pathology associated with AMHR-II, comprising an anticancer agent and an antibody binding AMHR-II, in which the humanized 12G4 monoclonal antibody is a fragment of the humanized 12G4 monoclonal antibody produced by the clone 3C-23K.

In a particular aspect, the invention relates to a composition for use as a medicinal product in the prevention or treatment of a pathology associated with AMHR-II, comprising an anticancer agent and an antibody binding AMHR-II, in which the antibody is a recombinant antibody produced by animal transgenesis.

In a particular aspect, the invention relates to a composition for use as a medicinal product in the prevention or treatment of a pathology associated with AMHR-II, comprising an anticancer agent and an antibody binding AMHR-II, in which the pathology associated with the human anti-Müllerian hormone type II receptor (AMHR-II) is cancer, and particularly ovarian cancer.

In a particular aspect, the invention relates to a composition for use as a medicinal product in the prevention or treatment of a pathology associated with AMHR-II, comprising an anticancer agent and an antibody binding AMHR-II, in which the anticancer agent is paclitaxel or a platinum salt selected from the group constituted by: oxaliplatin, cisplatin, carboplatin.

In a particular aspect, the invention relates to a composition for use as a medicinal product in the prevention or treatment of a pathology associated with AMHR-II, comprising an anticancer agent and an antibody binding AMHR-II, in which the anticancer agent is carboplatin.

In a particular aspect, the invention relates to a composition for use as a medicinal product in the prevention or treatment of a pathology associated with AMHR-II, comprising an anticancer agent and an antibody binding AMHR-II, in which the anticancer agent is paclitaxel.

In a particular aspect, the invention relates to a composition for use as a medicinal product in the prevention or treatment of a pathology associated with AMHR-II, comprising the 12G4 monoclonal antibody produced by the 3C23K clone and carboplatin.

In another particular aspect, the invention relates to a composition for use as a medicinal product in the prevention or treatment of a pathology associated with AMHR-II, comprising the 12G4 monoclonal antibody produced by the 3C23K clone and paclitaxel.

In another particular aspect, the invention relates to a composition for use as a medicinal product in the prevention or treatment of a pathology associated with AMHR-II, comprising an anticancer agent and an antibody binding AMHR-II, in a formulation intended for administration by the intravenous or intraperitoneal route.

In another particular aspect, the invention relates to a composition for use as a medicinal product in the prevention or treatment of a pathology associated with AMHR-II, comprising an anticancer agent and an antibody binding AMHR-II, the monoclonal antibody and the anticancer agent being intended for separate, simultaneous or sequential administration.

The antibody and the anticancer agent may be combined within one and the same pharmaceutical composition, or may be used in the form of separate pharmaceutical compositions, which may be administered simultaneously or sequentially. In particular, the products may be administered separately, namely either concomitantly, or independently, for example with a time gap.

More particularly, the invention relates to a composition for use as a medicinal product in the prevention or treatment of a pathology associated with AMHR-II, comprising an anticancer agent and an antibody binding AMHR-II, in which the antibody and the anticancer agent are combined within the same pharmaceutical composition.

According to another particular aspect, the invention relates to a composition for use as a medicinal product in the prevention or treatment of a pathology associated with AMHR-II, comprising an anticancer agent and an antibody binding AMHR-II, in which the therapeutically effective quantity of antibody administered to a patient is in a range from about 0.07 mg to about 35 000 mg, preferably from about 0.7 mg to about 7000 mg, preferably from about 0.7 mg to about 1400 mg, preferably from about 0.7 mg to about 700 mg, and more preferably from about 0.7 mg to about 70 mg.

According to another particular aspect, the invention relates to a composition for use as a medicinal product in the prevention or treatment of a pathology associated with AMHR-II, comprising an anticancer agent and an antibody binding AMHR-II, in which the therapeutically effective quantity of anticancer agent administered to a patient is in a range from about 10 mg to about 700 mg, preferably in a range from about 20 mg to about 350 mg, and preferably about 110 mg.

According to another particular aspect, the invention relates to a composition for use as a medicinal product in the prevention or treatment of a pathology associated with AMHR-II, comprising an anticancer agent and an antibody binding AMHR-II, in which the therapeutically effective quantity of antibody administered to a patient is about 70 mg and the dose of anticancer agent administered to the patient is about 110 mg.

In a preferred embodiment, the dosage of anticancer agent, in particular carboplatin or paclitaxel, is in a range from about 0.01 mg/kg to about 500 mg/kg, for example 0.1 mg/kg to 300 mg/kg, or from about 0.1 mg to 20 g per day.

As a variant, a higher initial loading dose, followed by one or more lower doses may also be administered. In another variant, an initial loading dose that is not so high, followed by one or more higher doses may also be administered.

In a particular embodiment, the anti-AMHR-II antibody and carboplatin may be used in an antibody/carboplatin ratio in a range from about 10/1 to about 0.1/1, in particular from about 10/1 to about 1/1, or from about 1/1 to about 0.1/1.

In another particular embodiment, the anti-AMHR-II antibody and paclitaxel may be used in an antibody/paclitaxel ratio in a range from about 10/1 to about 0.1/1, in particular from about 10/1 to about 1/1, or from about 1/1 to about 0.1/1.

The invention further relates to a product comprising an antibody binding the human anti-Müllerian hormone type II receptor (AMHR-II) and an anticancer agent, in the form of a combined preparation, for simultaneous, sequential or separate use as a medicinal product intended for preventing or treating a pathology associated with the human anti-Müllerian hormone type II receptor (AMHR-II), in particular cancer, and more particularly ovarian cancer.

According to a particular aspect, the invention relates to a product comprising an antibody binding the human anti-Müllerian hormone type II receptor (AMHR-II) and an anticancer agent, in the form of a combined preparation, for simultaneous, sequential or separate use as a medicinal product intended for preventing or treating a pathology associated with the human anti-Müllerian hormone type II receptor (AMHR-II), in particular cancer, and more particularly ovarian cancer, for simultaneous use of the antibody and of the anticancer agent.

According to another particular aspect, the invention relates to a product comprising an antibody binding the human anti-Müllerian hormone type II receptor (AMHR-II) and an anticancer agent, in the form of a combined preparation, for simultaneous, sequential or separate use as a medicinal product intended for preventing or treating a pathology associated with the human anti-Müllerian hormone type II receptor (AMHR-II), in particular cancer, and more particularly ovarian cancer, for sequential use of the antibody and of the anticancer agent, in which the antibody is administered prior to the anticancer agent.

According to another particular aspect, the invention relates to a product comprising an antibody binding the human anti-Müllerian hormone type II receptor (AMHR-II) and an anticancer agent, in the form of a combined preparation, for simultaneous, sequential or separate use as a medicinal product intended for preventing or treating a pathology associated with the human anti-Müllerian hormone type II receptor (AMHR-II), in particular cancer, and more particularly ovarian cancer, for sequential use of the antibody and of the anticancer agent, in which the anticancer agent is administered prior to the antibody.

The following figures, tables and examples illustrate the invention, without limiting its scope.

FIG. 1A shows the variation of the mean tumour volumes, expressed in $mm^3$, on the y-axis, as a function of the number of days counting from the day of injection of the tumour cells. FIG. 1B shows the curve of the median tumour volumes in $mm^3$, on the y-axis, as a function of the number of days counting from the day of injection of the tumour cells. In each of the graphs, the curve joining the filled squares represents the mean value of the mice in the control group, the continuous curve joining the diamonds represents the group of mice treated with the irrelevant antibody LFB-R565, the curve joining the filled triangles represents the group of mice treated with the 3C23K antibody, the continuous curve joining the filled circles represents the group of mice treated with carboplatin, the dotted curve joining the filled circles represents the group of mice treated with carboplatin and with the irrelevant antibody LFB-R565, the dotted curve joining the filled triangles represents the group of mice treated with carboplatin and with the 3C23K antibody.

FIGS. 2A to 2F show the curves of the individual tumour volumes, by groups. For each of the graphs 2A to 2F, the x-axis shows the number of days counting from the day of injection of the tumour cells, and the y-axis shows the tumour volume, each of the curves show the evolution of tumour volume for one animal. FIG. 2A shows the control group of mice, FIG. 2B shows the group of mice treated with the irrelevant antibody LFB-R565, FIG. 2C shows the group of mice treated with the 3C23K antibody, FIG. 2D shows the group of mice treated with carboplatin, FIG. 2E shows the group of mice treated with carboplatin and with the irrelevant antibody, FIG. 2F shows the group of mice treated with carboplatin and with the 3C23K antibody.

FIGS. 3A, 3B and 3C show the variation of the mean tumour volumes (3A) or the median tumour volumes (3B) and percentage survival, in 4 groups of mice treated respectively with the 3C23K antibody in monotherapy, paclitaxel in monotherapy or the combination of the 3C23K antibody and paclitaxel. A solution of NaCl was used as the control. FIG. 3A shows the variation of the mean the tumour volumes, expressed in $mm^3$, on the y-axis, as a function of the number of days counting from the day of injection of the tumour cells. FIG. 3B shows the curve of the median tumour volumes in $mm^3$, on the y-axis, as a function of the number of days counting from the day of injection of the tumour cells. FIG. 3C shows the respective percentage survival for the four groups, on the y-axis, as a function of the number of days counting from the day of injection of the tumour cells. In FIGS. 3A to 3C: the curves joining the diamonds correspond to the group treated with the control solution; the curves joining the squares correspond to the group treated with the 3C23K antibody in monotherapy; the curves joining the round dots correspond to the group treated with paclitaxel; the curves joining the triangles correspond to the group treated with the combination of the 3C23K antibody and paclitaxel.

FIGS. 4A, 4B, 4C and 4D show respectively the curve of the individual tumour volumes in 4 groups of mice treated respectively with the control solution (4A), the 3C23K antibody in monotherapy (4B), paclitaxel in monotherapy (4C), or the combination of the 3C23K antibody and paclitaxel (4D).

Table 1 gives a summary of the treatment schedule.

Table 2 gives a summary of the raw data for individual tumour volume.

Table 3 gives a summary of the raw data for mean tumour volume and standard deviation (SD).

Table 4 gives the raw data for the median tumour volumes and T/C ratio.

Table 5 gives a statistical analysis of the tumour volumes.

Table 6 gives a summary of the raw data for individual body weight.

Table 7 gives a summary of the raw data for mean body weight and standard deviation (SD).

Table 8 gives a summary of the raw data for individual body weight.

Table 9 gives a summary of the raw data for individual tumour volume.

Table 10 gives a summary of the raw data for the change in mean body weight.

Table 11 gives a summary of the raw data for the mean tumour volumes.

Table 12 gives a summary of the raw data for the median tumour volumes and for the T/C ratios.

Table 13 gives the results of statistical analysis.

Table 14 gives a summary of the raw data for the survival parameter

Table 15 gives the survival parameters

EXAMPLE

Evaluation of the Activity of the Antibody Produced by the 3C23K Clone (3C23K Antibody), in Monotherapy or in Combination with Carboplatin, in a Model of Human Ovarian Cancer Cov434-AMHRII Asc1a5 in the Female Swiss Nude Mouse 1. Protocol Female Swiss nude mice (Harlan Laboratories) were injected subcutaneously (s.c.) with $7.10^6$ cells of Cov434-AMHRII Asc1a5 (cell line of human ovarian cancer transfected with cDNA AMHRII) in Matrigel (1:1 ratio) under a volume of 150 µL on day 0 (D0).

The 3C23K antibody was evaluated according to the following scheme: 2 times per week for 6 weeks, for a total of 12 injections at about 10 mg/kg/injection, said administration regimen being designated below as "Q3-4D12". Another group of mice was treated with an irrelevant antibody LFB-R565, administered at about 10 mg/kg/injection, according to the regimen Q3-4D12.

Carboplatin was evaluated, at a sub-optimum dose, i.e. about 60 mg/kg/injection, according to the following scheme: once a week, for 4 weeks, said administration regimen being designated below as "Q7D4".

Carboplatin was also evaluated in combination with the 3C23K antibody or with the irrelevant antibody LFB-R565. Carboplatin was administered at about 60 mg/kg/injection according to the Q7D4 regimen and the 3C23K antibody or the irrelevant antibody LFB-R565 at about 10 mg/kg/injection according to the regimen Q3-4D12.

The mice were randomized on D11, when the volume of the tumours was between 50 and 158 mm$^3$, and the treatments began on D13 (9 mice per group). The description of the treatment dates is presented in Table 1.

In the context of evaluating the activity of the combination of the 3C23K antibody and paclitaxel relative to that of the 3C23K antibody in monotherapy or of paclitaxel in monotherapy, the 3C23K antibody was injected according to the following regimen: once weekly for 4 weeks, for a total of 4 injections, at a dose of about 10 mg/kg/injection according to the Q7D4 regimen; paclitaxel was injected according to the following regimen: once weekly for 4 weeks, for a total of 4 injections, at a dose of about 15 mg/kg/injection (Q7D4 regimen).

The mice were randomized on D13, when the volume of the tumours was between 58 and 150 mm$^3$, and the treatments began on D14 (8 mice per group).

a. Monitoring the Experiments in vivo

The tumours were usually measured twice weekly. Tumour volume (TV) was calculated using the following formula, in which the length corresponds to the largest of the tumour diameters, the width corresponds to the smallest of the tumour diameters and the tumour height: TV (mm$^3$)=(length×width×height)/2.

The curves of the individual volume of the tumours were plotted.

In addition, for each group, curves of tumour growth were plotted using the calculated mean tumour volumes or the median tumour volumes.

The animals were sacrificed when the tumour volumes reached 2000 mm$^3$ or for ethical reasons. The curves of mean values and median values as well as the statistical analyses were stopped when 20% of the mice in the group were dead.

In one experiment with 9 mice per group, the curves and analyses were therefore stopped when fewer than 8 values per group had been obtained (8 mice alive).

In one experiment with 8 mice per group, the curves and analyses were stopped when fewer than 7 values per group had been obtained (7 mice alive).

b. Evaluation of the Efficacy of the Treatment

Inhibition of tumour growth, defined as the ratio between the median tumour volumes of the treated mice relative to the treated control groups (T/C) was calculated as follows:

$$T/C = (\text{mean } TV \text{ of the treated group/mean } TV \text{ of the control group}) \times 100$$

The National Cancer Institute used the following criteria for evaluating the anti-tumour activity of a product (Bissery et al., 1991):

T/C greater than 42%, the product is considered to be ineffective

T/C between 42% and 10%, the product displays an anti-tumour effect

T/C less than 10%, the product is really effective.

Moreover, to identify whether the treatment has a toxic effect, the weight of the mice was monitored individually once a week. The mean body weight of the mice was calculated for each group, until 20% of the mice in the group were dead.

c. Statistical Analyses

The statistical differences between the different groups were analysed by ANOVA comparison using the Statgraphics centurion XV software.

The ANOVA table breaks down the variance into two components: an inter-group component and an intra-group component. The ratio F is the ratio of the inter-group estimate to the intra-group estimate. When the P value of test F is greater than or equal to 0.05, there is no statistically significant difference between the mean values of the two groups, with a confidence level of 95%. P values less than 0.05 indicate a significant difference between the mean values of the two groups with a confidence level of 95%.

The raw data of the statistical analyses in experiments with the F ratio and P value are presented in the appendix for all the experiments.

A Kruskal-Wallis test was also carried out. When the P value is greater than or equal to 0.05, there is no statistically significant difference between the median of the two groups, with a confidence level of 95%. P values less than 0.05 indicate a significant difference between the medians of the two groups with a confidence level of 95%.

2. Results 2.1 Evaluation of Anti-Tumour Activity of the 3C23K Antibody in Combinations with Carboplatin It appears that the 3C23K antibody or 3C23K displays significant anti-tumour activity compared to the control (NaCl solution) and to the LFB-R565 antibody (or LFB-R565) (FIGS. 1 and 2; Tables 2, 3, 4 and 5). Relative to the control, the 3C23K T/C ratios decreased from D14 to D36, on D18 the T/C ratio was 33% and was constantly less than 23% up to D36 (Table 4). Relative to the irrelevant antibody LFB-R565, the T/C ratios decreased from D14 to D36, on D18 the T/C ratio was 41% and was constantly less than 26% up to D36 (Table 4).

Figure 2:
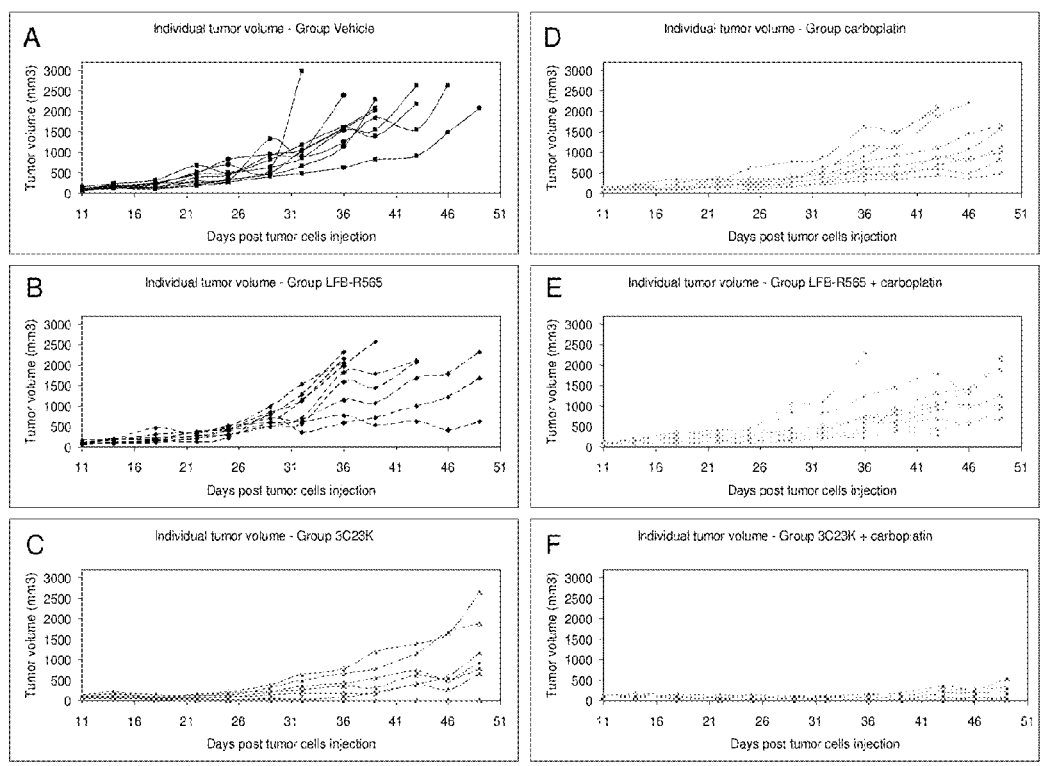

Moreover, the treatment with the irrelevant antibody LFB-R565 does not display anti-tumour activity relative to the control (FIGS. 1 and 2; Tables 2, 3, 4 and 5) since the T/C ratios were never less than 68% (Table 4).

Carboplatin also displays significant anti-tumour activity compared to the control or to the irrelevant antibody LFB- R565 (FIGS. 1 and 2; Tables 2, 3, 4 and 5). From D18 to D36, the T/C ratios relative to the control decreased gradually and the value was 40% on D36, indicating an anti-tumour activity (Table 4). Similarly, when compared to a group treated with the irrelevant antibody LFB-R565, the T/C ratio decreased from D25 to D36, reaching 35% on D36 (Table 4).

Results similar to those for the group treated with carboplatin were obtained with the combination carboplatin+LFB-R565, compared to the control group. From D18 to D36, the T/C ratios decreased gradually and, on D36, the T/C ratio was 40%, demonstrating an anti-tumour activity (Table 4).

When the group treated with carboplatin+LFB-R565 was regarded as the treated group and was compared to LFB-R565 alone, a decrease in the T/C ratios was observed starting from D22 and two T/C ratios less than 42% were found, on D25 and D36 (Table 4).

Moreover, there was no difference between the groups treated with carboplatin+LFB-R565 or with carboplatin alone (FIG. 1; Tables 2, 3, 4 and 5).

3C23K (10 mg/kg, Q3-4D12) and carboplatin (60 mg/kg, Q7D4) used in monotherapy showed an anti-tumour effect in this Cov434-AMHRII Asc1a5 xenografted tumour model at the doses tested (FIGS. 1 and 2; Tables 2, 3, 4 and 5).

Moreover, in the test conditions, 3C23K showed an anti-tumour effect greater than carboplatin. In fact, the T/C ratio of the group treated with 3C23K relative to the group treated with carboplatin decreased from D14 to D39, and from D22 to D39 the T/C ratios were less than 42%, which indicates an anti-tumour activity of 3C23K greater than that of carboplatin (Table 4).

When the group treated with carboplatin combined with 3C23K was compared to a control group, the combination showed a very strong anti-tumour effect: on D18 the T/C ratio was 24% and from D22 to D36 the T/C ratios were less than 10% (FIGS. 1 and 2; Tables 2, 3, 4 and 5).

Moreover, the combination of carboplatin (60 mg/kg, Q7D4) and 3C23K (10 mg/kg, Q3-4D12) showed an anti-tumour effect stronger than each of the components, 3C23K (10 mg/kg, Q3-4D12) or carboplatin (60 mg/kg, Q7D4) used in monotherapy (FIGS. 1 and 2; Tables 2, 3, 4 and 5).

In fact, when the group treated with carboplatin+3C23K was compared with the group treated with carboplatin, the combination showed a greater anti-tumour activity: on D14 the T/C ratio began to decrease and from D25 to D43 the calculated ratio was less than 11%.

Moreover, when the group treated with 3C23K and carboplatin was compared to the group treated with 3C23K, the combination showed an anti-tumour activity greater than that of the monotherapy with 3C23K. On D18, the T/C ratio began to decrease, and was found to be less than 42% between D22 and D29, which indicates an anti-tumour advantage, and was found to be less than 11% between D32 and D49, which indicates a large anti-tumour advantage (FIGS. 1 and 2; Tables 2, 3, 4 and 5).

Moreover, the group treated with carboplatin and 3C23K also showed an anti-tumour advantage compared to carboplatin combined with an irrelevant antibody LFB-R565 (Table 4).

The treatments had no effect until day 32 (Tables 6 and 7). On D32, a transient decrease in body weight was observed for the groups treated with carboplatin, carboplatin+LFB-R565 and carboplatin+3C23K. This decrease, after the third injection of carboplatin, on D28, was not greater than 15%, in comparison with the previous measurements on D25. The decrease was similar for the groups treated with carboplatin or carboplatin+LFB-R565 (about 15%) and was about 1% for the group treated with carboplatin+3C23K. In these three groups, the decrease in weight, slight and transient, was not regarded as a toxic effect as it was not confirmed after the 4th injection of carboplatin, on D34 (Tables 6 and 7).

3. Conclusions

In the present study the inventors evaluated the combination of 3C23K at 10 mg/kg, Q3-4D12, and the sub-optimum dose of carboplatin 60 mg/kg, Q7D4, on female nude mouse models with the Cov434-AMHRII Asc1a5 xenografted tumour, compared to a control group. An irrelevant antibody, LFB-R565 (10 mg/kg, Q3-4D12), was also tested, alone or in combination with carboplatin.

The results demonstrate that carboplatin (60 mg/kg Q7D4) exerts anti-tumour activity on Cov434-AMHRII Asc1a5. The results also demonstrate that 3C23K (10 mg/kg Q3-4D12) exerts anti-tumour activity on Cov434-AMHRII Asc1a5.

However, the anti-tumour activity observed with carboplatin alone was lower than that observed with 3C23K alone (10 mg/kg, Q3-4D12).

The combination of 3C23K and carboplatin was demonstrated as displaying an advantage when compared to 3C23K alone or to carboplatin alone and as a minimum had an additive effect.

Finally, the anti-tumour activity of 3C23K alone or in combination with carboplatin is specific, as no efficacy was observed with an irrelevant antibody, whether alone or in combination.

TABLE 1

Summary of the treatment schedule
Treatment schedule

| Date | Product | control vehicle | LFB-R565 | 3C23K | Carboplatin or carboplatin | carboplatin + LFB-R565 | carboplatin + 3C23K |
|---|---|---|---|---|---|---|---|
| 19-sep | D11 | | | | Randomization of the animals | | |
| 20-sep | D12 | | | | | | |
| 21-sep | D13 | TT | TT | TT | | TT | TT |
| 22-sep | D14 | | | | TT | TT | TT |
| 23-sep | D15 | TT | TT | TT | | TT | TT |
| 24-sep | D16 | | | | | | |
| 25-sep | D17 | | | | | | |
| 26-sep | D18 | TT | TT | TT | | TT | TT |
| 27-sep | D19 | | | | | | |
| 28-sep | D20 | | | | | | |
| 29-sep | D21 | | | | TT | TT | TT |
| 30-sep | D22 | TT | TT | TT | | TT | TT |

TABLE 1-continued

Summary of the treatment schedule
Treatment schedule

| Date | Product | control vehicle | LFB-R565 | 3C23K | Carboplatin or carboplatin | carboplatin + LFB-R565 | carboplatin + 3C23K |
|---|---|---|---|---|---|---|---|
| 01-oct | D23 | | | | | | |
| 02-oct | D24 | | | | | | |
| 03-oct | D25 | TT | TT | TT | | TT | TT |
| 04-oct | D26 | | | | | | |
| 05-oct | D27 | | | | | | |
| 06-oct | D28 | | | | TT | TT | TT |
| 07-oct | D29 | TT | TT | TT | | TT | TT |
| 08-oct | D30 | | | | | | |
| 09-oct | D31 | | | | | | |
| 10-oct | D32 | TT | TT | TT | | TT | TT |
| 11-oct | D33 | | | | | | |
| 12-oct | D34 | | | | | | |
| 13-oct | D35 | | | | TT | TT | TT |
| 14-oct | D36 | TT | TT | TT | | TT | TT |
| 15-oct | D37 | | | | | | |
| 16-oct | D38 | | | | | | |
| 17-oct | D39 | TT | TT | TT | | TT | TT |
| 18-oct | D40 | | | | | | |
| 19-oct | D41 | | | | | | |
| 20-oct | D42 | | | | | | |
| 21-oct | D43 | TT | TT | TT | | TT | TT |
| 22-oct | D44 | | | | | | |
| 23-oct | D45 | | | | | | |
| 24-oct | D46 | TT | TT | TT | | TT | TT |
| 25-oct | D47 | | | | | | |
| 26-oct | D48 | | | | | | |
| 27-oct | D49 | | | | | | |

TABLE 2

Summary of the raw data for individual tumour volume
Individual tumour volume

| Group | Mouse number | Sep. 19, 2011 D11 | Sep. 22, 2011 D14 | Sep. 26, 2011 D18 | Sep. 30, 2011 D22 | Oct. 3, 2011 D25 | Oct. 7, 2011 D29 | Oct. 10, 2011 D32 | Oct. 14, 2011 D36 | Oct. 17, 2011 D39 | Oct. 21, 2011 D43 | Oct. 24, 2011 D46 | Oct. 27, 2011 D49 |
|---|---|---|---|---|---|---|---|---|---|---|---|---|---|
| NaCl | 1-SM | 91 | 126 | 250 | 504 | 819 | 952 | 1020 | 2404 | | | | |
| | 1-OD | 72 | 169 | 143 | 297 | 303 | 1320 | 891 | 1260 | 1848 | 1564 | 2622 | |
| | 1-OG | 96 | 147 | 216 | 520 | 700 | 588 | 2993 | | | | | |
| | 1-2O | 107 | 180 | 240 | 468 | 480 | 644 | 864 | 1540 | 1560 | 2625 | | |
| | 1-2OD | 99 | 192 | 144 | 216 | 330 | 462 | 660 | 1144 | 2280 | | | |
| | 2-SM | 60 | 163 | 248 | 252 | 336 | 504 | 1045 | 1617 | 2070 | | | |
| | 2-OD | 74 | 120 | 135 | 392 | 441 | 936 | 1053 | 1589 | 2024 | | | |
| | 2-OG | 158 | 234 | 324 | 672 | 495 | 819 | 1181 | 1607 | 1386 | 2178 | | |
| | 2-2O | 77 | 123 | 108 | 180 | 1264 | 420 | 490 | 630 | 828 | 912 | 1485 | 2080 |
| LFB-R565 | 3-SM | 90 | 203 | 173 | 378 | 432 | 792 | 1287 | 2321 | | | | |
| | 3-OD | 72 | 110 | 140 | 126 | 216 | 792 | 356 | 588 | 720 | 995 | 1215 | 1672 |
| | 3-OG | 96 | 154 | 297 | 360 | 465 | 840 | 1140 | 2166 | 2166 | | | |
| | 3-2O | 153 | 175 | 460 | 324 | 520 | 588 | 690 | 1824 | 1790 | 2112 | | |
| | 3-2OD | 108 | 154 | 192 | 363 | 504 | 980 | 1536 | 2052 | | | | |
| | 4-SM | 58 | 176 | 216 | 270 | 385 | 585 | 1122 | 1980 | 2576 | | | |
| | 4-OD | 72 | 110 | 140 | 197 | 410 | 693 | 616 | 774 | 528 | 624 | 413 | 630 |
| | 4-OG | 81 | 95 | 108 | 216 | 297 | 504 | 569 | 1584 | 1454 | 2079 | | |
| | 4-2O | 60 | 95 | 160 | 270 | 288 | 504 | 660 | 1144 | 1073 | 1672 | 1785 | 2321 |
| 3C23K | 5-SM | 98 | 104 | 72 | 60 | 0 | 0 | 0 | 0 | 0 | 0 | 0 | 0 |
| | 5-OD | 90 | 179 | 88 | 150 | 126 | 322 | 501 | 653 | 784 | 1171 | 1683 | 1870 |
| | 5-OG | 61 | 60 | 36 | 30 | 0 | 27 | 27 | 87 | 210 | 420 | 598 | 1188 |
| | 5-2O | 80 | 72 | 21 | 0 | 0 | 0 | 0 | 0 | 0 | 0 | 0 | 0 |
| | 5-2OD | 57 | 67 | 41 | 36 | 24 | 48 | 15 | 0 | 0 | 0 | 0 | 0 |
| | 6-SM | 147 | 216 | 140 | 131 | 180 | 225 | 275 | 363 | 315 | 631 | 504 | 784 |
| | 6-OD | 113 | 166 | 80 | 77 | 74 | 146 | 180 | 182 | 182 | 393 | 275 | 655 |
| | 6-OG | 72 | 84 | 72 | 158 | 216 | 385 | 644 | 784 | 1200 | 1403 | 1650 | 2646 |
| | 6-2O | 72 | 53 | 53 | 70 | 88 | 210 | 350 | 432 | 546 | 731 | 518 | 945 |
| carboplatin | 7-SM | 53 | 104 | 98 | 378 | 140 | 270 | 351 | 630 | 660 | 864 | 1071 | 1568 |
| | 7-OD | 142 | 210 | 173 | 126 | 240 | 200 | 243 | 424 | 484 | 592 | 501 | 819 |
| | 7-OG | 61 | 162 | 112 | 360 | 270 | 360 | 578 | 1148 | 1134 | 1881 | 2205 | |
| | 7-2O | 102 | 210 | 336 | 324 | 616 | 768 | 864 | 1610 | 1495 | 2112 | | |
| | 7-2OD | 90 | 126 | 248 | 363 | 152 | 360 | 653 | 893 | 1488 | 2038 | | |
| | 8-SM | 72 | 123 | 140 | 270 | 358 | 363 | 504 | 462 | 447 | 882 | 810 | 1125 |

TABLE 2-continued

Summary of the raw data for individual tumour volume
Individual tumour volume

| Group | Mouse number | Sep. 19, 2011 D11 | Sep. 22, 2011 D14 | Sep. 26, 2011 D18 | Sep. 30, 2011 D22 | Oct. 3, 2011 D25 | Oct. 7, 2011 D29 | Oct. 10, 2011 D32 | Oct. 14, 2011 D36 | Oct. 17, 2011 D39 | Oct. 21, 2011 D43 | Oct. 24, 2011 D46 | Oct. 27, 2011 D49 |
|---|---|---|---|---|---|---|---|---|---|---|---|---|---|
| | 8-OD | 81 | 75 | 90 | 156 | 98 | 168 | 220 | 308 | 347 | 438 | 378 | 480 |
| | 8-OG | 70 | 134 | 112 | 198 | 243 | 420 | 462 | 774 | 910 | 1105 | 1450 | 1650 |
| | 8-2O | 114 | 168 | 90 | 168 | 210 | 187 | 275 | 594 | 423 | 672 | 878 | 980 |
| LFB-R565 + carboplatin | 9-SM | 116 | 203 | 216 | 297 | 298 | 420 | 518 | 720 | 936 | 1323 | 1440 | 2112 |
| | 9-OD | 72 | 90 | 123 | 126 | 112 | 180 | 385 | 594 | 608 | 900 | 965 | 1233 |
| | 9-OG | 63 | 90 | 126 | 112 | 91 | 144 | 180 | 350 | 501 | 429 | 592 | 686 |
| | 9-2O | 102 | 150 | 180 | 220 | 170 | 330 | 336 | 726 | 564 | 675 | 570 | 936 |
| | 9-2OD | 98 | 168 | 299 | 420 | 432 | 1040 | 1134 | 2288 | | | | |
| | 10-SM | 51 | 210 | 193 | 210 | 264 | 410 | 455 | 704 | 774 | 1008 | 1378 | 1881 |
| | 10-OD | 130 | 180 | 338 | 280 | 193 | 865 | 798 | 1232 | 1449 | 1783 | 1320 | 2185 |
| | 10-OG | 68 | 72 | 85 | 135 | 123 | 192 | 266 | 462 | 840 | 1081 | 995 | 995 |
| | 10-2O | 81 | 90 | 98 | 108 | 117 | 210 | 248 | 216 | 378 | 293 | | |
| 3C23K + carboplatin | 11-SM | 63 | 168 | 140 | 120 | 105 | 96 | 88 | 70 | 45 | 165 | 175 | 189 |
| | 11-OD | 123 | 102 | 54 | 38 | 24 | 40 | 18 | 0 | 24 | 66 | 69 | 90 |
| | 11-OG | 83 | 95 | 45 | 24 | 23 | 35 | 45 | 48 | 50 | | | |
| | 11-2O | 83 | 96 | 53 | 24 | 18 | 81 | 18 | 18 | 0 | 18 | 23 | 24 |
| | 11-2OD | 123 | 112 | 112 | 24 | 0 | 0 | 0 | 18 | 0 | 18 | 34 | 81 |
| | 12-SM | 50 | 84 | 18 | 0 | 0 | 0 | 0 | 18 | 11 | 24 | 23 | 28 |
| | 12-OD | 72 | 77 | 47 | 72 | 54 | 108 | 88 | 140 | 100 | 242 | 250 | 325 |
| | 12-OG | 107 | 158 | 21 | 0 | 0 | 32 | 0 | 0 | 0 | 24 | 42 | 45 |
| | 12-2O | 65 | 60 | 72 | 98 | 132 | 112 | 105 | 160 | 184 | 357 | 273 | 539 |

TABLE 3

Summary of the raw data for mean tumour volume and standard deviation (SD)
Mean tumour volume

| Group | | 11 | 14 | 18 | 22 | 25 | 29 | 32 | 36 | 39 | 43 | 46 | 49 |
|---|---|---|---|---|---|---|---|---|---|---|---|---|---|
| Control | Mean | 93 | 161 | 201 | 389 | 463 | 738 | 1133 | 1474 | | | | |
| | SD | 10 | 13 | 25 | 58 | 67 | 104 | 258 | 191 | | | | |
| LFB-R565 | Mean | 10 | 14 | 38 | 31 | 37 | 58 | 140 | 222 | | | | |
| | SD | 10 | 21 | 12 | 20 | 29 | 51 | 84 | 105 | 146 | 181 | 233 | 321 |
| 3C23K | Mean | 88 | 111 | 67 | 79 | 79 | 151 | 221 | 278 | 360 | 528 | 581 | 899 |
| | SD | 10 | 21 | 12 | 20 | 29 | 51 | 84 | 105 | 146 | 181 | 233 | 321 |
| carboplatin | Mean | 87 | 146 | 155 | 260 | 258 | 344 | 461 | 760 | 821 | 1176 | | |
| | SD | 10 | 16 | 30 | 35 | 55 | 65 | 76 | 145 | 161 | 232 | | |
| LFB-R565 + carboplatin | Mean | 87 | 139 | 184 | 212 | 200 | 421 | 480 | 810 | 756 | 936 | | |
| | SD | 9 | 19 | 31 | 37 | 40 | 113 | 108 | 221 | 127 | 183 | | |
| 3C23K + carboplatin | Mean | 85 | 106 | 62 | 44 | 40 | 56 | 40 | 53 | 46 | 114 | 111 | 165 |
| | SD | 9 | 12 | 13 | 14 | 16 | 15 | 14 | 20 | 21 | 46 | 38 | 65 |

TABLE 4

Raw data for median tumour volumes and T/C ratios

| | 11 | 14 | 18 | 22 | 25 | 29 | 32 | 36 | 39 | 43 | 46 | 49 |
|---|---|---|---|---|---|---|---|---|---|---|---|---|
| Mean tumour volume | | | | | | | | | | | | |
| Control | 91 | 163 | 216 | 392 | 441 | 644 | 1020 | 1564 | | | | |
| LFB-R565 | 81 | 154 | 173 | 270 | 410 | 693 | 690 | 1824 | | | | |
| 3C23K | 80 | 84 | 72 | 70 | 74 | 146 | 180 | 182 | 210 | 420 | 504 | 784 |
| carboplatin | 81 | 134 | 112 | 270 | 240 | 360 | 462 | 630 | 660 | 882 | | |
| LFB-R565 + carboplatin | 81 | 150 | 180 | 210 | 170 | 330 | 385 | 704 | 691 | 954 | | |
| 3C23K + carboplatin | 83 | 96 | 53 | 24 | 23 | 40 | 18 | 18 | 24 | 45 | 55 | 86 |
| TC ratio (%) | | | | | | | | | | | | |
| Control-LFB-R565 | 89 | 95 | 80 | 69 | 93 | 108 | 68 | 117 | | | | |
| Control-3C23K | 88 | 52 | 33 | 18 | 17 | 23 | 18 | 12 | | | | |
| Control-carboplatin | 89 | 82 | 52 | 69 | 54 | 56 | 45 | 40 | | | | |
| Control-LFB-R565 + carboplatin | 89 | 92 | 83 | 54 | 39 | 51 | 38 | 45 | | | | |
| Control-3C23K + carboplatin | 91 | 59 | 24 | 6 | 5 | 6 | 2 | 1 | | | | |

TABLE 4-continued

Raw data for median tumour volumes and T/C ratios

| | Day | | | | | | | | | | | |
|---|---|---|---|---|---|---|---|---|---|---|---|---|
| | 11 | 14 | 18 | 22 | 25 | 29 | 32 | 36 | 39 | 43 | 46 | 49 |
| LFB-R565-3C23K | 99 | 55 | 41 | 26 | 18 | 21 | 26 | 10 | | | | |
| LFB-R565-carboplatin | 100 | 87 | 65 | 100 | 59 | 52 | 67 | 35 | | | | |
| LFB-R565-LFB-R565 + carboplatin | 100 | 97 | 104 | 78 | 42 | 48 | 56 | 39 | | | | |
| LFB-R565-3C23K + carboplatin | 102 | 63 | 30 | 9 | 5 | 6 | 3 | 1 | | | | |
| carboplatin-3C23K | 99 | 63 | 64 | 26 | 31 | 41 | 39 | 29 | 32 | 48 | | |
| carboplatin-LFB-R565 + carboplatin | 100 | 112 | 161 | 78 | 71 | 92 | 83 | 112 | 105 | 108 | | |
| carboplatin-3C23K + carboplatin | 102 | 72 | 47 | 9 | 9 | 11 | 4 | 3 | 4 | 5 | | |
| 3C23K-3C23K + carboplatin | 103 | 115 | 73 | 34 | 31 | 27 | 10 | 10 | 11 | 11 | 11 | 11 |
| LFB-R565 + carboplatin-3C23K + carboplatin | 102 | 64 | 29 | 11 | 13 | 12 | 5 | 3 | 3 | 5 | | |

TABLE 5

Statistical analysis of the tumour volumes
Statistical analysis of the tumour volumes

| Day | Groups | F ratio | P value | Sign. | Test statistic | P value | Sign. |
|---|---|---|---|---|---|---|---|
| D11 | Control-LFB-R565 | 0.13 | 0.73 | | 0.44 | 0.51 | |
| | Control-3C23K | 0.13 | 0.72 | | 0.33 | 0.57 | |
| | Control-carboplatin | 0.16 | 0.69 | | 0.28 | 0.60 | |
| | Control-LFB-R565 + carboplatin | 0.21 | 0.66 | | 0.12 | 0.72 | |
| | Control-3C23K + carboplatin | 0.31 | 0.59 | | 0.24 | 0.63 | |
| | LFB-R565-3C23K | 0.00 | 1.00 | | 0.00 | 1.00 | |
| | LFB-R565-carboplatin | 0.00 | 0.97 | | 0.00 | 0.96 | |
| | LFB-R565-LFB-R565 + carboplatin | 0.01 | 0.94 | | 0.01 | 0.93 | |
| | LFB-R565-3C23K + carboplatin | 0.03 | 0.86 | | 0.00 | 0.96 | |
| | carboplatin-3C23K | 0.00 | 0.97 | | 0.00 | 0.96 | |
| | carboplatin-LFB-R565 + carboplatin | 0.00 | 0.97 | | 0.00 | 1.00 | |
| | carboplatin-3C23K + carboplatin | 0.02 | 0.89 | | 0.00 | 1.00 | |
| | 3C23K-LFB-R565 + carboplatin | 0.01 | 0.94 | | 0.01 | 0.93 | |
| | 3C23K-3C23K + carboplatin | 0.03 | 0.86 | | 0.00 | 0.96 | |
| | LFB-R565 + carboplatin-3C23K + carboplatin | 0.01 | 0.92 | | 0.00 | 0.96 | |
| D14 | Control-LFB-R565 | 1.23 | 0.28 | | 1.22 | 0.27 | |
| | Control-3C23K | 4.54 | 0.05 | * | 3.60 | 0.06 | |
| | Control-carboplatin | 0.64 | 0.44 | | 0.57 | 0.45 | |
| | Control-LFB-R565 + carboplatin | 1.03 | 0.32 | | 0.63 | 0.43 | |
| | Control-3C23K + carboplatin | 10.41 | 0.01 | * | 7.74 | 0.01 | * |
| | LFB-R565-3C23K | 1.57 | 0.23 | | 1.88 | 0.17 | |
| | LFB-R565-carboplatin | 0.05 | 0.83 | | 0.10 | 0.76 | |
| | LFB-R565-LFB-R565 + carboplatin | 0.01 | 0.93 | | 0.20 | 0.66 | |
| | LFB-R565-3C23K + carboplatin | 3.96 | 0.06 | | 2.98 | 0.08 | |
| | carboplatin-3C23K | 1.88 | 0.19 | | 2.00 | 0.16 | |
| | carboplatin-LFB-R565 + carboplatin | 0.08 | 0.79 | | 0.13 | 0.72 | |
| | carboplatin-3C23K + carboplatin | 4.26 | 0.06 | | 3.78 | 0.05 | * |
| | 3C23K-LFB-R565 + carboplatin | 1.08 | 0.31 | | 1.76 | 0.18 | |
| | 3C23K-3C23K + carboplatin | 0.05 | 0.82 | | 0.10 | 0.76 | |
| | LFB-R565 + carboplatin-3C23K + carboplatin | 2.39 | 0.14 | | 1.13 | 0.29 | |
| D18 | Control-LFB-R565 | 0.04 | 0.84 | | 0.05 | 0.83 | |
| | Control-3C23K | 25.29 | 0.00 | * | 11.57 | 0.00 | * |
| | Control-carboplatin | 1.51 | 0.24 | | 2.26 | 0.13 | |
| | Control-LFB-R565 + carboplatin | 0.19 | 0.67 | | 0.63 | 0.43 | |
| | Control-3C23K + carboplatin | 25.53 | 0.00 | * | 10.96 | 0.00 | * |
| | LFB-R565-3C23K | 14.01 | 0.00 | * | 11.62 | 0.00 | * |
| | LFB-R565-carboplatin | 1.39 | 0.26 | | 2.27 | 0.13 | |
| | LFB-R565-LFB-R565 + carboplatin | 0.29 | 0.59 | | 0.20 | 0.66 | |
| | LFB-R565-3C23K + carboplatin | 14.50 | 0.00 | * | 11.01 | 0.00 | * |
| | carboplatin-3C23K | 8.37 | 0.01 | * | 9.59 | 0.00 | * |
| | carboplatin-LFB-R565 + carboplatin | 0.50 | 0.49 | | 0.78 | 0.38 | |
| | carboplatin-3C23K + carboplatin | 8.86 | 0.01 | * | 7.54 | 0.01 | * |
| | 3C23K-LFB-R565 + carboplatin | 13.69 | 0.00 | * | 9.84 | 0.00 | * |
| | 3C23K-3C23K + carboplatin | 0.07 | 0.80 | | 0.20 | 0.66 | |
| | LFB-R565 + carboplatin-3C23K + carboplatin | 14.18 | 0.00 | * | 9.28 | 0.00 | * |
| D22 | Control-LFB-R565 | 3.19 | 0.09 | | 2.00 | 0.16 | |
| | Control-3C23K | 28.51 | 0.00 | * | 12.79 | 0.00 | * |
| | Control-carboplatin | 4.01 | 0.06 | | 3.28 | 0.07 | |
| | Control-LFB-R565 + carboplatin | 7.35 | 0.02 | * | 5.28 | 0.02 | * |
| | Control-3C23K + carboplatin | 36.82 | 0.00 | * | 12.86 | 0.00 | * |
| | LFB-R565-3C23K | 33.73 | 0.00 | * | 10.98 | 0.00 | * |
| | LFB-R565-carboplatin | 0.17 | 0.69 | | 0.13 | 0.72 | |
| | LFB-R565-LFB-R565 + carboplatin | 2.12 | 0.16 | | 1.76 | 0.18 | |

TABLE 5-continued

Statistical analysis of the tumour volumes

| Day | Groups | F ratio | P value | Sign. | Test statistic | P value | Sign. |
|---|---|---|---|---|---|---|---|
| | LFB-R565-3C23K + carboplatin | 52.97 | 0.00 | * | 12.87 | 0.00 | * |
| | carboplatin-3C23K | 22.58 | 0.00 | * | 10.39 | 0.00 | * |
| | carboplatin-LFB-R565 + carboplatin | 0.99 | 0.33 | | 1.12 | 0.29 | |
| | carboplatin-3C23K + carboplatin | 35.55 | 0.00 | * | 12.86 | 0.00 | * |
| | 3C23K-LFB-R565 + carboplatin | 11.13 | 0.00 | * | 6.79 | 0.01 | * |
| | 3C23K-3C23K + carboplatin | 2.19 | 0.16 | | 2.14 | 0.14 | |
| | LFB-R565 + carboplatin-3C23K + carboplatin | 19.45 | 0.00 | * | 11.62 | 0.00 | * |
| D25 | Control-LFB-R565 | 1.02 | 0.33 | | 0.44 | 0.51 | |
| | Control-3C23K | 31.60 | 0.00 | * | 12.84 | 0.00 | * |
| | Control-carboplatin | 6.33 | 0.02 | * | 6.33 | 0.01 | * |
| | Control-LFB-R565 + carboplatin | 12.96 | 0.00 | * | 9.56 | 0.00 | * |
| | Control-3C23K + carboplatin | 42.71 | 0.00 | * | 12.84 | 0.00 | * |
| | LFB-R565-3C23K | 50.07 | 0.00 | * | 12.54 | 0.00 | * |
| | LFB-R565-carboplatin | 4.51 | 0.05 | * | 5.07 | 0.02 | * |
| | LFB-R565-LFB-R565 + carboplatin | 13.94 | 0.00 | * | 7.50 | 0.01 | * |
| | LFB-R565-3C23K + carboplatin | 83.99 | 0.00 | * | 12.84 | 0.00 | * |
| | carboplatin-3C23K | 9.51 | 0.01 | * | 8.27 | 0.00 | * |
| | carboplatin-LFB-R565 + carboplatin | 0.84 | 0.37 | | 0.86 | 0.35 | |
| | carboplatin-3C23K + carboplatin | 16.39 | 0.00 | * | 11.61 | 0.00 | * |
| | 3C23K-LFB-R565 + carboplatin | 6.89 | 0.02 | * | 5.09 | 0.02 | * |
| | 3C23K-3C23K + carboplatin | 1.54 | 0.23 | | 0.73 | 0.39 | |
| | LFB-R565 + carboplatin-3C23K + carboplatin | 15.49 | 0.00 | * | 9.87 | 0.00 | * |
| D29 | Control-LFB-R565 | 0.13 | 0.72 | | 0.00 | 1.00 | |
| | Control-3C23K | 28.90 | 0.00 | * | 12.80 | 0.00 | * |
| | Control-carboplatin | 11.64 | 0.00 | * | 9.57 | 0.00 | * |
| | Control-LFB-R565 + carboplatin | 4.78 | 0.04 | * | 5.28 | 0.02 | * |
| | Control-3C23K + carboplatin | 47.26 | 0.00 | * | 12.80 | 0.00 | * |
| | LFB-R565-3C23K | 56.20 | 0.00 | * | 12.83 | 0.00 | * |
| | LFB-R565-carboplatin | 18.53 | 0.00 | * | 9.86 | 0.00 | * |
| | LFB-R565-LFB-R565 + carboplatin | 5.30 | 0.04 | * | 4.31 | 0.04 | * |
| | LFB-R565-3C23K + carboplatin | 127.11 | 0.00 | * | 12.83 | 0.00 | * |
| | carboplatin-3C23K | 6.17 | 0.02 | * | 4.31 | 0.04 | * |
| | carboplatin-LFB-R565 + carboplatin | 0.39 | 0.54 | | 0.03 | 0.86 | |
| | carboplatin-3C23K + carboplatin | 21.04 | 0.00 | * | 12.82 | 0.00 | * |
| | 3C23K-LFB-R565 + carboplatin | 5.32 | 0.03 | * | 4.13 | 0.04 | * |
| | 3C23K-3C23K + carboplatin | 3.64 | 0.07 | | 1.44 | 0.23 | |
| | LFB-R565 + carboplatin-3C23K + carboplatin | 11.49 | 0.00 | * | 12.80 | 0.00 | * |
| D32 | Control-LFB-R565 | 0.80 | 0.39 | | 0.20 | 0.66 | |
| | Control-3C23K | 12.70 | 0.00 | * | 11.57 | 0.00 | * |
| | Control-carboplatin | 7.03 | 0.02 | * | 9.56 | 0.00 | * |
| | Control-LFB-R565 + carboplatin | 6.13 | 0.02 | * | 7.25 | 0.01 | * |
| | Control-3C23K + carboplatin | 20.13 | 0.00 | * | 12.87 | 0.00 | * |
| | LFB-R565-3C23K | 18.68 | 0.00 | * | 10.40 | 0.00 | * |
| | LFB-R565-carboplatin | 8.06 | 0.01 | * | 6.33 | 0.01 | * |
| | LFB-R565-LFB-R565 + carboplatin | 5.95 | 0.03 | * | 5.48 | 0.02 | * |
| | LFB-R565-3C23K + carboplatin | 40.84 | 0.00 | * | 12.87 | 0.00 | * |
| | carboplatin-3C23K | 5.03 | 0.04 | * | 4.13 | 0.04 | * |
| | carboplatin-LFB-R565 + carboplatin | 0.02 | 0.88 | | 0.05 | 0.83 | |
| | carboplatin-3C23K + carboplatin | 33.41 | 0.00 | * | 12.87 | 0.00 | * |
| | 3C23K-LFB-R565 + carboplatin | 3.99 | 0.06 | | 3.13 | 0.08 | |
| | 3C23K-3C23K + carboplatin | 5.01 | 0.04 | * | 1.92 | 0.17 | |
| | LFB-R565 + carboplatin-3C23K + carboplatin | 18.20 | 0.00 | * | 12.87 | 0.00 | * |
| D36 | Control-LFB-R565 | 0.22 | 0.65 | | 0.28 | 0.60 | |
| | Control-3C23K | 36.45 | 0.00 | * | 10.76 | 0.00 | * |
| | Control-carboplatin | 10.34 | 0.01 | * | 6.03 | 0.01 | * |
| | Control-LFB-R565 + carboplatin | 5.70 | 0.03 | * | 5.33 | 0.02 | * |
| | Control-3C23K + carboplatin | 70.67 | 0.00 | * | 12.07 | 0.00 | * |
| | LFB-R565-3C23K | 32.80 | 0.00 | * | 11.01 | 0.00 | * |
| | LFB-R565-carboplatin | 11.39 | 0.00 | * | 6.12 | 0.01 | * |
| | LFB-R565-LFB-R565 + carboplatin | 7.22 | 0.02 | * | 5.07 | 0.02 | * |
| | LFB-R565-3C23K + carboplatin | 54.44 | 0.00 | * | 12.86 | 0.00 | * |
| | carboplatin-3C23K | 8.19 | 0.01 | * | 5.50 | 0.02 | * |
| | carboplatin-LFB-R565 + carboplatin | 0.04 | 0.84 | | 0.02 | 0.89 | |
| | carboplatin-3C23K + carboplatin | 26.34 | 0.00 | * | 12.86 | 0.00 | * |
| | 3C23K-LFB-R565 + carboplatin | 5.33 | 0.03 | * | 5.09 | 0.02 | * |
| | 3C23K-3C23K + carboplatin | 4.99 | 0.04 | * | 1.68 | 0.19 | |
| | LFB-R565 + carboplatin-3C23K + carboplatin | 13.13 | 0.00 | * | 12.86 | 0.00 | * |
| D39 | carboplatin-3C23K | 5.05 | 0.04 | * | 4.70 | 0.03 | * |
| | carboplatin-LFB-R565 + carboplatin | 0.11 | 0.75 | | 0.00 | 1.00 | |
| | carboplatin-3C23K + carboplatin | 25.47 | 0.00 | * | 12.84 | 0.00 | * |
| | 3C23K-LFB-R565 + carboplatin | 4.64 | 0.05 | * | 4.50 | 0.03 | * |
| | 3C23K-3C23K + carboplatin | 5.08 | 0.04 | * | 2.34 | 0.13 | |
| | LFB-R565 + carboplatin-3C23K + carboplatin | 39.24 | 0.00 | * | 12.06 | 0.00 | * |

TABLE 5-continued

Statistical analysis of the tumour volumes
Statistical analysis of the tumour volumes

| Day | Groups | F ratio | P value | Sign. | Test statistic | P value | Sign. |
|---|---|---|---|---|---|---|---|
| D43 | carboplatin-3C23K | 5.46 | 0.03 | * | 4.32 | 0.04 | * |
| | carboplatin-LFB-R565 + carboplatin | 0.72 | 0.41 | | 0.33 | 0.56 | |
| | carboplatin-3C23K + carboplatin | 20.12 | 0.00 | * | 12.03 | 0.00 | * |
| | 3C23K-LFB-R565 + carboplatin | 2.85 | 0.11 | | 2.38 | 0.12 | |
| | LFB-R565 + carboplatin-3C23K + carboplatin | 21.66 | 0.00 | * | 10.63 | 0.00 | * |
| | 3C23K-3C23K + carboplatin | 4.91 | 0.04 | * | 1.34 | 0.25 | |
| D46 | 3C23K-3C23K + carboplatin | 3.95 | 0.07 | | 1.34 | 0.25 | |
| D49 | 3C23K-3C23K + carboplatin | 5.02 | 0.04 | * | 1.34 | 0.25 | |

TABLE 6

Summary of the raw data for individual body weight
Individual body weight of the mice

| Group | Mouse number | Sep. 19, 2011 D11 | Sep. 26, 2011 D18 | Oct. 03, 2011 D25 | Oct. 10, 2011 D32 | Oct. 17, 2011 D39 | Oct. 24, 2011 D46 |
|---|---|---|---|---|---|---|---|
| NaCl | 1-SM | 25.6 | 27.3 | 28.2 | 29.2 | | |
| | 1-OD | 22.3 | 24.8 | 24.7 | 25.0 | 27.0 | 28.9 |
| | 1-OG | 25.0 | 27.6 | 28.0 | 29.0 | | |
| | 1-2O | 21.5 | 22.8 | 23.2 | 24.6 | 25.8 | |
| | 1-2OD | 25.0 | 27.0 | 28.1 | 29.6 | 29.6 | |
| | 2-SM | 22.4 | 23.6 | 23.8 | 25.4 | 27.1 | |
| | 2-OD | 24.0 | 26.1 | 26.8 | 29.3 | 30.0 | |
| | 2-OG | 22.8 | 22.0 | 23.8 | 25.6 | 25.0 | |
| | 2-2O | 24.4 | 24.4 | 25.2 | 27.0 | 27.1 | 29.6 |
| LFB-R565 | 3-SM | 23.4 | 23.3 | 24.0 | 25.1 | | |
| | 3-OD | 22.2 | 23.6 | 23.8 | 23.9 | 25.2 | 27.0 |
| | 3-OG | 23.5 | 24.4 | 24.8 | 25.8 | | |
| | 3-2O | 21.5 | 21.8 | 22.3 | 23.5 | 24.6 | |
| | 3-2OD | 25.4 | 25.6 | 26.4 | 28.2 | | |
| | 4-SM | 23.6 | 25.0 | 25.1 | 26.6 | 28.2 | |
| | 4-OD | 27.1 | 26.4 | 28.2 | 29.7 | 30.5 | 30.7 |
| | 4-OG | 23.2 | 24.1 | 24.6 | 26.3 | 26.8 | |
| | 4-2O | 24.9 | 26.0 | 26.0 | 29.7 | 30.4 | 32.8 |
| 3C23K | 5-SM | 21.0 | 22.1 | 22.1 | 22.6 | 23.1 | 22.5 |
| | 5-OD | 20.2 | 21.8 | 22.2 | 23.5 | 24.1 | 24.9 |
| | 5-OG | 25.8 | 26.6 | 26.6 | 27.0 | 27.2 | 27.2 |
| | 5-2O | 24.9 | 25.2 | 25.0 | 25.2 | 27.8 | 26.0 |
| | 5-2OD | 23.5 | 26.4 | 26.0 | 26.0 | 26.5 | 27.2 |
| | 6-SM | 21.4 | 21.8 | 22.3 | 23.0 | 23.8 | 23.3 |
| | 6-OD | 23.0 | 24.2 | 25.0 | 24.0 | 26.0 | 25.7 |
| | 6-OG | 23.9 | 24.5 | 25.8 | 25.8 | 27.9 | 28.9 |
| | 6-2O | 24.9 | 24.0 | 24.3 | 24.8 | 25.3 | 25.8 |
| carboplatin | 7-SM | 22.3 | 22.2 | 27.6 | 23.7 | 24.3 | 25.4 |
| | 7-OD | 25.8 | 24.6 | 28.3 | 24.5 | 23.9 | 25.7 |
| | 7-OG | 23.0 | 22.6 | 25.6 | 23.6 | 25.1 | 26.4 |
| | 7-2O | 27.1 | 26.1 | 32.7 | 28.0 | 27.2 | |
| | 7-2OD | 23.3 | 24.4 | 27.0 | 23.1 | 25.4 | |
| | 8-SM | 24.5 | 25.4 | 29.4 | 23.1 | 22.4 | 25.7 |
| | 8-OD | 22.7 | 23.6 | 25.6 | 21.1 | 20.0 | 21.7 |
| | 8-OG | 20.4 | 20.3 | 24.2 | 20.2 | 21.0 | 21.0 |
| | 8-2O | 22.3 | 22.0 | 26.0 | 23.6 | 23.3 | 25.0 |
| LFB-R565 + carboplatin | 9-SM | 22.2 | 21.8 | 26.2 | 20.9 | 22.7 | 23.1 |
| | 9-OD | 22.4 | 22.9 | 26.9 | 18.3 | 22.3 | 22.8 |
| | 9-OG | 24.0 | 23.9 | 27.7 | 23.0 | 23.8 | 24.8 |
| | 9-2O | 18.9 | 19.2 | 23.5 | 22.2 | 19.1 | 19.8 |
| | 9-2OD | 21.5 | 22.9 | 27.1 | 21.8 | | |
| | 10-SM | 23.0 | 22.6 | 23.9 | 22.7 | 25.3 | 24.3 |
| | 10-OD | 25.2 | 25.4 | 26.6 | 26.1 | 25.6 | 27.8 |
| | 10-OG | 25.8 | 25.3 | 28.2 | 27.0 | 26.2 | 27.5 |
| | 10-2O | 23.4 | 23.3 | 23.6 | 21.4 | 18.6 | |
| 3C23K + carboplatin | 11-SM | 26.8 | 26.8 | 26.3 | 27.0 | 26.9 | 27.5 |
| | 11-OD | 21.3 | 21.5 | 22.6 | 22.8 | 21.4 | 23.2 |
| | 11-OG | 20.0 | 19.2 | 20.1 | 18.8 | 17.0 | |
| | 11-2O | 24.0 | 24.8 | 23.1 | 24.0 | 23.1 | 25.0 |
| | 11-2OD | 24.6 | 23.5 | 22.9 | 25.2 | 22.5 | 24.0 |
| | 12-SM | 21.8 | 23.7 | 24.0 | 22.5 | 21.0 | 22.5 |
| | 12-OD | 22.3 | 20.5 | 23.7 | 22.7 | 22.3 | 23.7 |

TABLE 6-continued

Summary of the raw data for individual body weight
Individual body weight of the mice

| Group | Mouse number | Sep. 19, 2011 D11 | Sep. 26, 2011 D18 | Oct. 03, 2011 D25 | Oct. 10, 2011 D32 | Oct. 17, 2011 D39 | Oct. 24, 2011 D46 |
|---|---|---|---|---|---|---|---|
| | 12-OG | 22.7 | 24.2 | 24.4 | 23.1 | 21.6 | 22.8 |
| | 12-2O | 22.8 | 21.9 | 25.0 | 23.6 | 23.6 | 25.2 |

TABLE 7

Summary of the raw data for mean
body weight and standard deviation (SD).
Mean body weight of the mice

| Group | | Day | | | | | |
|---|---|---|---|---|---|---|---|
| | | 11 | 18 | 25 | 32 | 39 | 46 |
| Control | Mean | 23.7 | 25.1 | 25.8 | 27.2 | | |
| | SD | 1.5 | 2.0 | 2.0 | 2.1 | | |
| LFB-R565 | Mean | 23.9 | 24.5 | 25.0 | 26.5 | | |
| | SD | 1.7 | 1.5 | 1.7 | 2.3 | | |
| 3C23K | Mean | 23.2 | 24.1 | 24.4 | 24.7 | 25.7 | 25.7 |
| | SD | 1.9 | 1.9 | 1.8 | 1.5 | 1.8 | 2.0 |
| carboplatin | Mean | 23.5 | 23.5 | 27.4 | 23.4 | 23.6 | |
| | SD | 2.0 | 1.8 | 2.5 | 2.2 | 2.2 | |
| LFB-R565 + carboplatin | Mean | 22.9 | 23.0 | 26.0 | 22.6 | 23.0 | |
| | SD | 2.1 | 1.9 | 1.8 | 2.6 | 2.9 | |
| 3C23K + carboplatin | Mean | 22.9 | 22.9 | 23.6 | 23.3 | 22.2 | 24.2 |
| | SD | 2.0 | 2.3 | 1.7 | 2.2 | 2.6 | 1.6 |

2.2 Evaluation of an Anti-Tumour Activity of the 3C23K Antibody in Combination with Paclitaxel The 3C23K antibody and paclitaxel are evaluated in vivo in monotherapy or in combination in the mice that received the injection of Cov434-AMHRII Asc1a5 tumour cells (a cell line of human ovarian cancer). The treatment is initiated on day 14 after injection.

Figure 3:
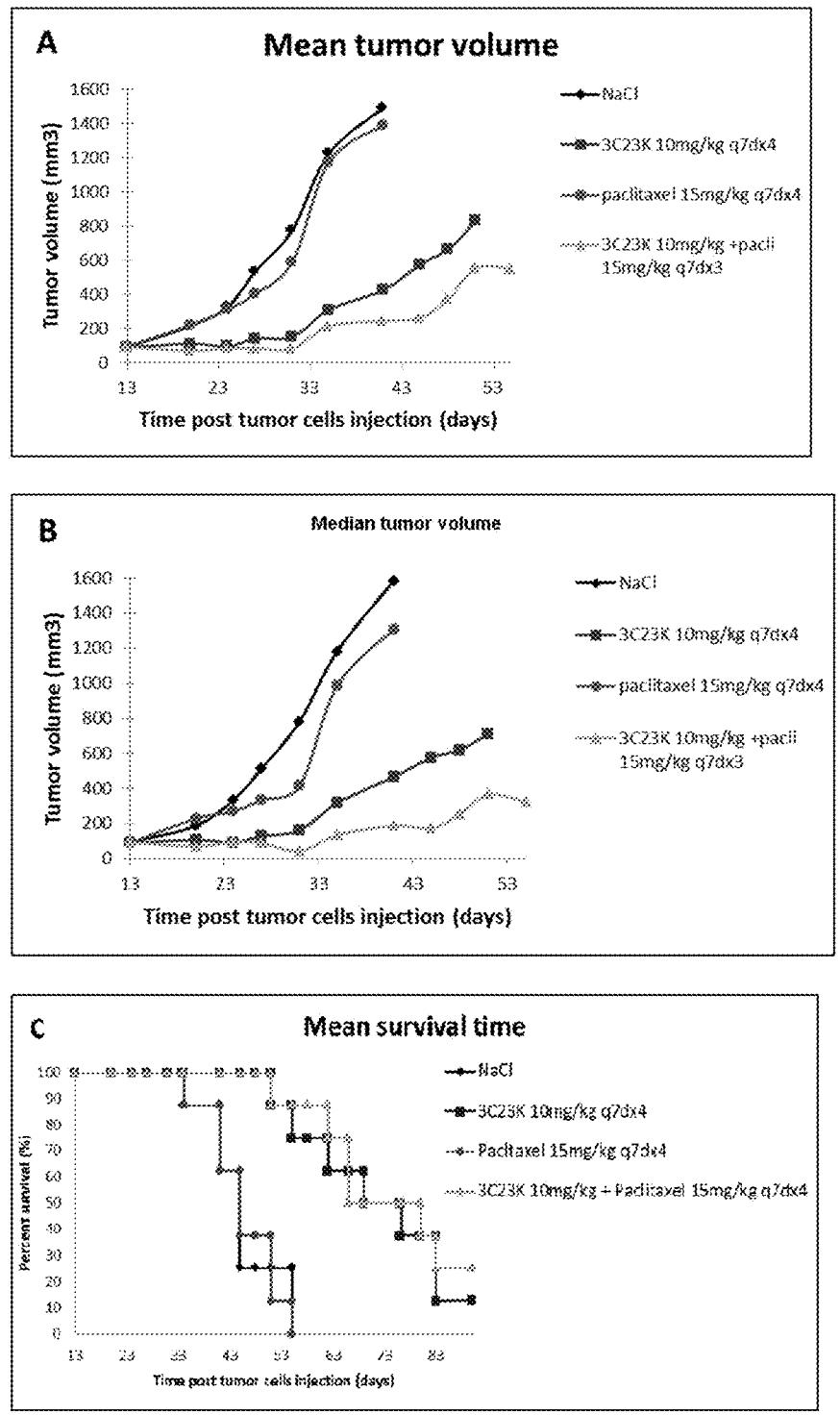
Figure 4:
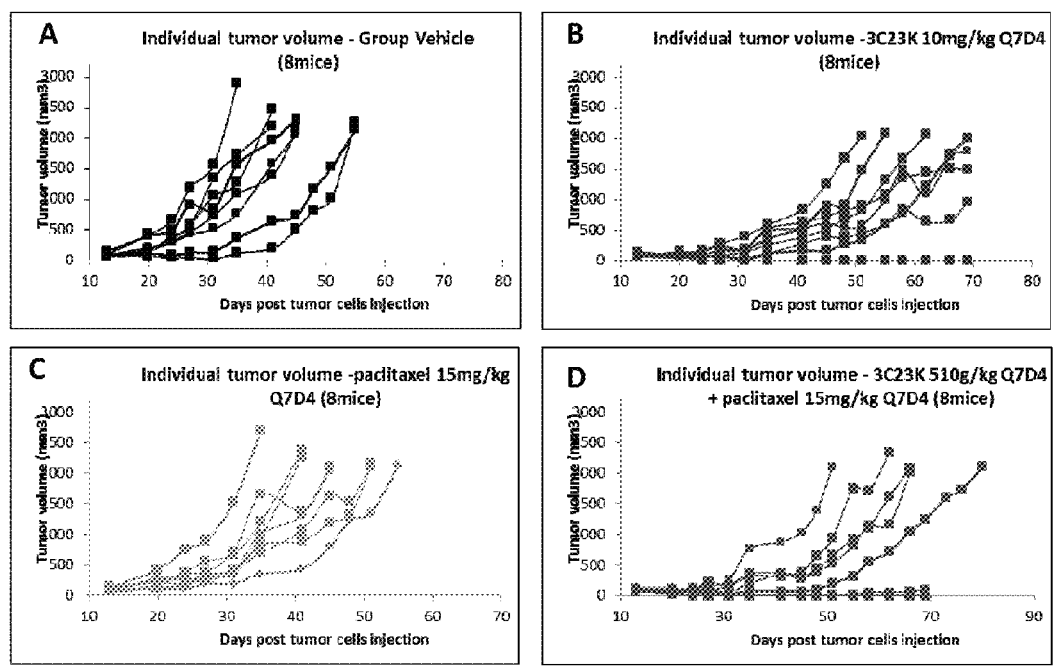

It was observed that the 3C23K antibody administered at 10 mg/kg according to the Q7D4 regimen described above displays significant anti-tumour activity compared to a control solution (NaCl solution) (FIGS. 3 and 4; Tables 9, 11, 12, 13, 14 and 15).

Relative to the group treated with the control solution, the T/C ratios of the group treated with the 3C23K antibody decreased starting from D20. On D20 the T/C ratio was 57% and was constantly less than 29% up to D40 (Table 12).

Paclitaxel alone only shows a modest inhibition of tumour growth compared to the control solution. From D24 to D41, the T/C ratio changes from 83% to 53%.

Compared to the control, a greater anti-tumour activity was obtained in the group treated with the combination of the 3C23K antibody and paclitaxel (FIGS. 3 and 4; Tables 9, 11, 12, 13 14 and 15). The T/C ratio was less than 38% on D20 and was always less than 28% up to D41 (Table 12). Moreover, the T/C ratio on D31, D35 and D41 was 6%, 11% and 12% respectively. Compared to the result described by Bissery et al. in 1991, the results of the present invention show that the T/C ratio was around and less than 10% between D31 and D41, indicating that treatment with a combination of the 3C23K antibody and paclitaxel is an effective therapy.

Moreover, the 3C23K antibody administered at 10 mg/kg according to the Q7D4 regimen showed an anti-tumour effect greater than that of paclitaxel. In fact, the T/C ratio of the group treated with 3C23K relative to the group treated with paclitaxel decreased starting from D20. The T/C ratio on D20 was 47% and was less than 39% on D41 (Table 12), which indicates an anti-tumour activity of 3C23K greater than that of paclitaxel.

The combination of the 3C23K antibody (10 mg/kg, Q7D4) and paclitaxel (15 mg/kg, Q7D4 regimen) showed an anti-tumour effect stronger than each of the components, 3C23K (10 mg/kg, Q7D4) or paclitaxel (15 mg/kg, Q7D4 regimen) used in monotherapy.

In fact, when the group treated with the aforesaid combination was compared with the group treated with paclitaxel, the combination showed a greater anti-tumour activity: on D20 the T/C ratio began to decrease and the ratio was 31% on D20 and was less than 35% up to D41 (Table 12).

When the group treated with the aforesaid combination was compared with the group treated with the 3C23K antibody, the combination showed an anti-tumour activity greater than that of monotherapy with 3C23K. On D31, the T/C ratio began to decrease, the T/C ratio was 27% on D31 and was less than 42% up to D48 (Table 12). On D51, the T/C ratio is only 51%, nevertheless indicating a difference between these two groups, as 49% inhibition of tumour growth was observed (Table 12).

Statistical analysis of tumour volume confirms the results of analysis of the T/C ratio.

The 3C23K antibody in monotherapy and the 3C23K antibody in combination with paclitaxel show a significant anti-tumour activity compared to that of the control (NaCl solution) starting from D20 to D41 (Table 13).

Paclitaxel in monotherapy does not have an activity that is significantly different from that of the control (Table 13).

The 3C23K antibody in monotherapy displays an anti-tumour activity that is significantly different from that of paclitaxel in monotherapy starting from D20 to D41 (Table 13).

Compared to the paclitaxel treatment in monotherapy, treatment with the combination of the 3C23K antibody and paclitaxel displays a better anti-tumour activity starting from D20 to D41 (Table 13).

Statistical analysis based on the survival parameter also confirms the results for the T/C ratio and analysis of tumour volume.

The 3C23K antibody in monotherapy and the combination of the 3C23K antibody and paclitaxel respectively show a significant anti-tumour activity compared to that of the control (Table 15).

Paclitaxel in monotherapy does not have an activity that is significantly different from that of the control (Table 15).

The 3C23K antibody in monotherapy displays an anti-tumour activity that is significantly different from that of paclitaxel in monotherapy (Table 15). Compared to the paclitaxel treatment in monotherapy, treatment with the combination of the 3C23K antibody and paclitaxel displays a better anti-tumour activity (Table 15).

The treatments have no effect on body weight (Tables 8 and 10).

In conclusion, the combination of the 3C23K antibody and paclitaxel displays an advantage relative to 3C23K alone or to paclitaxel alone and as a minimum has an additive effect.

TABLE 8

Summary of the raw data for individual body weight
Individual body weight

| Group | Mouse number | D20 | D27 | D35 | D41 | D48 | D55 | D62 | D69 |
|---|---|---|---|---|---|---|---|---|---|
| Control | 1-SM | 23.4 | 24.1 | 26.0 | 26.9 | | | | |
| | 1-OD | 23.6 | 25.4 | 26.5 | | | | | |
| | 1-OG | 23.1 | 24.6 | 25.0 | 26.1 | | | | |
| | 1-2O | 21.8 | 23.4 | 25.2 | 25.4 | | | | |
| | 1-2OG | 23.7 | 25.8 | 26.8 | 27.8 | | | | |
| | 1-2OG/OD | 22.5 | 23.7 | 24.8 | 25.0 | | | | |
| | 10-2OD | 22.1 | 23.4 | 24.3 | 23.5 | 24.7 | 26.1 | | |
| | 10-2OG | 22.4 | 23.5 | 28.4 | 27.8 | 28.5 | 29.6 | | |
| 3C23K 10 mg/kg q7d4 | 2-SM | 21.3 | 21.8 | 23.0 | 22.4 | 23.3 | 24.6 | | |
| | 2-OD | 25.0 | 24.8 | 26.8 | 27.0 | 27.5 | | | |
| | 2-OG | 24.8 | 26.3 | 27.0 | 27.6 | 27.2 | 27.5 | | |
| | 2-2O | 23.7 | 25.0 | 25.4 | 27.0 | 25.4 | 25.5 | 26.6 | 26.6 |
| | 2-2OD | 25.5 | 26.3 | 26.7 | 27.0 | 26.8 | 26.9 | 27.6 | 27.7 |
| | 2-2OG | 27.1 | 26.9 | 28.7 | 29.2 | 28.7 | 28.0 | 28.2 | 28.6 |
| | 8-SM | 20.5 | 21.0 | 21.4 | 21.7 | 22.0 | 22.4 | 23.4 | |
| | 8-OD | 25.3 | 26.1 | 26.0 | 26.5 | 27.6 | 27.4 | 28.9 | 28.7 |
| Paclitaxel 15 mg/kg q7d4 | 6-SM | 25.6 | 27.1 | 30.7 | 0.0 | 0.0 | 0.0 | 0.0 | 0.0 |
| | 6-OD | 25.8 | 25.7 | 27.8 | 27.7 | 28.0 | 0.0 | 0.0 | 0.0 |
| | 6-OG | 24.5 | 24.3 | 26.2 | 26.5 | 0.0 | 0.0 | 0.0 | 0.0 |
| | 6-2O | 24.4 | 24.6 | 27.7 | 27.2 | 0.0 | 0.0 | 0.0 | 0.0 |
| | 6-2OD | 22.4 | 24.0 | 26.5 | 26.7 | 0.0 | 0.0 | 0.0 | 0.0 |
| | 6-2OG | 25.9 | 26.4 | 29.0 | 28.7 | 0.0 | 0.0 | 0.0 | 0.0 |
| | 10-SM | 24.8 | 25.0 | 26.8 | 27.1 | 26.8 | 0.0 | 0.0 | 0.0 |
| | 10-OD | 23.9 | 23.6 | 23.9 | 23.7 | 25.2 | 26.3 | 0.0 | 0.0 |
| 3C23K 10 mg/kg q7d4 + Paclitaxel 15 mg/kg q7d4 | 7-SM | 22.0 | 22.4 | 22.3 | 22.3 | 25.5 | 22.2 | 0.0 | 0.0 |
| | 7-OD | 26.4 | 26.8 | 26.8 | 25.7 | 26.7 | 28.3 | 29.4 | 0.0 |
| | 7-OG | 24.1 | 25.1 | 25.9 | 25.6 | 26.3 | 26.2 | 0.0 | 0.0 |
| | 7-2O | 22.0 | 22.2 | 23.7 | 23.4 | 25.1 | 0.0 | 0.0 | 0.0 |
| | 7-2OD | 22.4 | 22.6 | 24.3 | 26.0 | 24.4 | 25.8 | 26.6 | 0.0 |
| | 7-2OG | 22.5 | 23.6 | 25.0 | 25.0 | 24.9 | 26.7 | 27.6 | 0.0 |
| | 10-OG | 22.8 | 23.7 | 24.7 | 23.6 | 24.7 | 24.5 | 24.6 | 25.1 |
| | 10-2O | 22.7 | 23.7 | 24.4 | 23.8 | 24.7 | 25.0 | 25.4 | 26.8 |

TABLE 9

Summary of the raw data for individual tumour volume

| Group | | Day | | | | | | | | | |
|---|---|---|---|---|---|---|---|---|---|---|---|
| | | 13 | 20 | 24 | 27 | 31 | 35 | 41 | 45 | 48 | 51 |
| Control | 1-SM | 150 | 403 | 495 | 910 | 840 | 1566 | 1966 | 2320 | | |
| | 1-OD | 98 | 423 | 660 | 1190 | 1568 | 2898 | | | | |
| | 1-OG | 96 | 189 | 399 | 561 | 1344 | 1734 | 2200 | | | |
| | 1-2O | 90 | 210 | 297 | 423 | 520 | 770 | 1584 | 2058 | | |
| | 1-2OG | 74 | 187 | 358 | 576 | 1056 | 1276 | 2474 | | | |
| | 1-2OG/OD | 65 | 162 | 315 | 469 | 725 | 1089 | 1396 | 2128 | | |
| | 10-2OD | 106 | 72 | 41 | 50 | 24 | 117 | 197 | 510 | 819 | 1008 |
| | 10-2OG | 66 | 105 | 81 | 126 | 143 | 366 | 631 | 725 | 1170 | 1521 |
| 3C23K 10 mg/kg q7d4 | 2-SM | 144 | 105 | 158 | 252 | 184 | 366 | 560 | 918 | 912 | 1485 |
| | 2-OD | 98 | 135 | 180 | 289 | 404 | 592 | 844 | 1256 | 1672 | 2035 |
| | 2-OG | 98 | 88 | 0 | 0 | 0 | 0 | 0 | 0 | 0 | 0 |
| | 2-2O | 90 | 140 | 102 | 192 | 204 | 488 | 540 | 624 | 551 | 587 |
| | 2-2OD | 76 | 150 | 114 | 168 | 198 | 528 | 634 | 731 | 833 | 900 |
| | 2-2OG | 73 | 60 | 68 | 72 | 68 | 122 | 293 | 392 | 381 | 462 |
| | 8-SM | 88 | 105 | 84 | 90 | 140 | 268 | 394 | 529 | 689 | 837 |
| | 8-OD | 72 | 108 | 72 | 90 | 28 | 119 | 169 | 166 | 276 | 351 |
| Paclitaxel 15 mg/kg q7d4 | 6-SM | 126 | 424 | 756 | 896 | 1530 | 2706 | | | | |
| | 6-OD | 117 | 243 | 257 | 325 | 420 | 699 | 1064 | 1632 | 1536 | 2166 |
| | 6-OG | 98 | 240 | 356 | 386 | 673 | 1200 | 2380 | | | |
| | 6-2O | 83 | 280 | 284 | 255 | 410 | 1008 | 1309 | 2040 | | |
| | 6-2OD | 83 | 170 | 380 | 560 | 720 | 1653 | 1389 | 2112 | | |
| | 6-2OG | 66 | 126 | 180 | 347 | 410 | 965 | 2269 | | | |
| | 10-SM | 144 | 217 | 180 | 270 | 358 | 823 | 884 | 1197 | 1323 | 2112 |
| | 10-OD | 58 | 105 | 110 | 198 | 192 | 351 | 437 | 798 | 1232 | 1348 |
| 3C23K 10 mg/kg q7d4 + Paclitaxel 15 mg/kg q7d4 | 7-SM | 131 | 126 | 85 | 0 | 0 | 0 | 0 | 0 | 0 | 0 |
| | 7-OD | 116 | 105 | 112 | 223 | 160 | 324 | 315 | 390 | 655 | 938 |
| | 7-OG | 95 | 28 | 0 | 0 | 0 | 0 | 0 | 0 | 0 | 0 |
| | 7-2O | 88 | 70 | 142 | 150 | 264 | 768 | 875 | 1033 | 1400 | 2112 |
| | 7-2OD | 74 | 41 | 112 | 105 | 163 | 357 | 368 | 336 | 399 | 532 |

TABLE 9-continued

Summary of the raw data for individual tumour volume

| | | | | | | | | | | |
|---|---|---|---|---|---|---|---|---|---|---|
| | 7-2OG | 66 | 41 | 63 | 85 | 63 | 203 | 347 | 281 | 429 | 662 |
| | 10-OG | 110 | 96 | 104 | 96 | 0 | 0 | 0 | 0 | 0 | 0 |
| | 10-2O | 61 | 72 | 72 | 27 | 24 | 66 | 63 | 68 | 105 | 200 |

| | | Day | | | | | | | | |
|---|---|---|---|---|---|---|---|---|---|---|
| Group | | 55 | 58 | 62 | 66 | 69 | 73 | 76 | 80 | 83 |
| Control | 1-SM | | | | | | | | | |
| | 1-OD | | | | | | | | | |
| | 1-OG | | | | | | | | | |
| | 1-2O | | | | | | | | | |
| | 1-2OG | | | | | | | | | |
| | 1- | | | | | | | | | |
| | 10-2OD | 2268 | | | | | | | | |
| | 10-2OG | 2145 | | | | | | | | |
| 3C23K 10 mg/kg q7d4 | 2-SM | 2080 | | | | | | | | |
| | 2-OD | | | | | | | | | |
| | 2-OG | 0 | 0 | 0 | 0 | 0 | 0 | 0 | 0 | 0 |
| | 2-2O | 990 | 1482 | 1080 | 1695 | 1788 | 1820 | 2296 | | |
| | 2-2OD | 1084 | 1350 | 1440 | 1512 | 1496 | 1559 | 1238 | 1520 | 1615 |
| | 2-2OG | 600 | 842 | 640 | 666 | 950 | 1018 | 1140 | 1254 | 1463 |
| | 8-SM | 1309 | 1665 | 2057 | | | | | | |
| | 8-OD | 600 | 792 | 1215 | 1740 | 2000 | | | | |
| Paclitaxel 15 mg/kg q7d4 | 6-SM | | | | | | | | | |
| | 6-OD | | | | | | | | | |
| | 6-OG | | | | | | | | | |
| | 6-2O | | | | | | | | | |
| | 6-2OD | | | | | | | | | |
| | 6-2OG | | | | | | | | | |
| | 10-SM | | | | | | | | | |
| | 10-OD | 2132 | | | | | | | | |
| 3C23K 10 mg/kg q7d4 + Paclitaxel 15 mg/kg q7d4 | 7-SM | 0 | 0 | 0 | 0 | 0 | 0 | 0 | 0 | 0 |
| | 7-OD | 1755 | 1710 | 2340 | | | | | | |
| | 7-OG | 0 | 0 | 0 | 0 | 0 | 0 | 0 | 0 | 0 |
| | 7-2O | | | | | | | | | |
| | 7-2OD | 816 | 1140 | 1170 | 2016 | | | | | |
| | 7-2OG | 924 | 1109 | 1620 | 2081 | | | | | |
| | 10-OG | 24 | 53 | 50 | 60 | 96 | 189 | 192 | 347 | 413 |
| | 10-2O | 324 | 551 | 714 | 1040 | 1245 | 1604 | 1725 | 2112 | |

TABLE 10

Summary of the raw data for change in mean body weight

| | | Days | | | | | |
|---|---|---|---|---|---|---|---|
| Groups | | 20 | 27 | 35 | 41 | 48 | 55 |
| control | Mean | 22.83 | 24.24 | 25.88 | 26.07 | | |
| | SD | 0.72 | 0.94 | 1.34 | 1.57 | | |
| 3C23K 10 mg/kg q7d4 | Mean | 24.15 | 24.78 | 25.63 | 26.05 | 26.06 | 26.04 |
| | SD | 2.22 | 2.21 | 2.36 | 2.60 | 2.32 | 2.01 |
| Paclitaxel 15 mg/kg q7d4 | Mean | 24.66 | 25.09 | 27.33 | 26.80 | | |
| | SD | 1.17 | 1.22 | 2.02 | 1.55 | | |
| 3C23K 10 mg/kg q7d4 + Paclitaxel 15 mg/kg q7d4 | Mean | 23.11 | 23.76 | 24.64 | 24.43 | 25.29 | 25.53 |
| | SD | 1.48 | 1.54 | 1.36 | 1.33 | 0.82 | 1.91 |

TABLE 11

Summary of the raw data for the mean tumour volumes

| | | Days | | | | | | | | | |
|---|---|---|---|---|---|---|---|---|---|---|---|
| Groups | | 13 | 20 | 24 | 27 | 31 | 35 | 41 | 45 | 48 | 51 | 55 |
| Control | Mean | 93 | 219 | 331 | 538 | 777 | 1227 | 1492 | | | | |
| | SD | 10 | 48 | 77 | 142 | 205 | 331 | 339 | | | | |
| 3C23K 10 mg/kg q7dx4 | Mean | 92 | 111 | 97 | 144 | 153 | 310 | 429 | 577 | 664 | 832 | |
| | SD | 16 | 23 | 41 | 81 | 94 | 183 | 215 | 305 | 362 | 482 | |
| paclitaxel 15 mg/kg q7dx4 | Mean | 97 | 226 | 313 | 405 | 589 | 1176 | 1390 | | | | |
| | SD | 11 | 38 | 76 | 86 | 157 | 274 | 290 | | | | |
| 3C23K 10 mg/kg + paclitaxel 15 mg/kg q7dx4 | Mean | 92 | 72 | 86 | 86 | 84 | 215 | 246 | 263 | 373 | 555 | 549 |
| | SD | 9 | 13 | 16 | 29 | 38 | 101 | 114 | 132 | 182 | 272 | 269 |

TABLE 12

Summary of the raw data for the median tumour volumes and T/C ratios

| | Days | | | | | | | | | | |
|---|---|---|---|---|---|---|---|---|---|---|---|
| | 13 | 20 | 24 | 27 | 31 | 35 | 41 | 45 | 48 | 51 | 55 |
| Median tumour volume | | | | | | | | | | | |
| control | 93 | 188 | 336 | 515 | 782 | 1183 | 1584 | | | | |
| 3C23K 10 mg/kg q7dx4 | 89 | 107 | 93 | 129 | 162 | 317 | 467 | 577 | 620 | 712 | |
| paclitaxel 15 mg/kg q7dx4 | 90 | 228 | 270 | 336 | 415 | 986 | 1309 | | | | |
| 3C23K 10 mg/kg + paclitaxel 15 mg/kg q7dx4 | 91 | 71 | 94 | 90 | 44 | 134 | 189 | 174 | 252 | 366 | 324 |
| T/C ratio | | | | | | | | | | | |
| control-3C23K 10 mg/kg q7dx4 | | 95 | 57 | 28 | 25 | 21 | 27 | 29 | | | |
| control-paclitaxel 15 mg/kg q7dx4 | | 97 | 121 | 80 | 65 | 53 | 83 | 83 | | | |
| control-3C23K 10 mg/kg q7dx4 + paclitaxel 15 mg/kg q7dx4 | | 98 | 38 | 28 | 18 | 6 | 11 | 12 | | | |
| 3C23K 10 mg/kg q7dx4-paclitaxel 15 mg/kg q7dx4 | | 98 | 47 | 35 | 38 | 39 | 32 | 36 | | | |
| 3C23K 10 mg/kg q7dx4-3C23K 10 mg/kg q7dx4 + paclitaxel 15 mg/kg q7dx4 | | 103 | 67 | 101 | 70 | 27 | 42 | 40 | 30 | 41 | 51 |
| paclitaxel 15 mg/kg q7dx4-3C23K 10 mg/kg + paclitaxel 15 mg/kg q7dx4 | | 101 | 31 | 35 | 27 | 11 | 14 | 14 | | | |

TABLE 13

Statistical analysis

| Day | Contrast between groups | ANOVA | | | Kruskal - Wallis | | |
|---|---|---|---|---|---|---|---|
| | | F-ratio | P-value | Sig. | Test | P-value | Sig. |
| D13 | control-3C23K 10 mg/kg q7d4 | 0.00 | 0.95 | | 0.00 | 0.96 | |
| | control-paclitaxel 15 mg/kg q7d4 | 0.07 | 0.80 | | 0.04 | 0.83 | |
| | control-3C23K 10 mg/kg q7d4 + paclitaxel 15 mg/kg q7d4 | 0.00 | 0.97 | | 0.00 | 1.00 | |
| | 3C23K 10 mg/kg q7d4-paclitaxel 15 mg/kg q7d4 | 0.11 | 0.74 | | 0.03 | 0.87 | |
| | 3C23K 10 mg/kg q7d4-3C23K 10 mg/kg q7d4 + paclitaxel 15 mg/kg q7d4 | 0.00 | 0.98 | | 0.00 | 0.96 | |
| | paclitaxel 15 mg/kg q7d4-3C23K 10 mg/kg q7d4 + paclitaxel 15 mg/kg q7d4 | 0.09 | 0.76 | | 0.07 | 0.79 | |
| D20 | control-3C23K 10 mg/kg q7d4 | 5.33 | 0.04 | * | 4.44 | 0.04 | * |
| | control-paclitaxel 15 mg/kg q7d4 | 0.01 | 0.91 | | 0.47 | 0.49 | |
| | control-3C23K 10 mg/kg q7d4 + paclitaxel 15 mg/kg q7d4 | 9.71 | 0.01 | * | 8.08 | 0.00 | * |
| | 3C23K 10 mg/kg q7d4-paclitaxel 15 mg/kg q7d4 | 9.54 | 0.01 | * | 6.39 | 0.01 | * |
| | 3C23K 10 mg/kg q7d4-3C23K 10 mg/kg q7d4 + paclitaxel 15 mg/kg q7d4 | 5.84 | 0.03 | * | 4.44 | 0.04 | * |
| | paclitaxel 15 mg/kg q7d4-3C23K 10 mg/kg q7d4 + paclitaxel 15 mg/kg q7d4 | 16.67 | 0.00 | * | 9.97 | 0.00 | * |
| D24 | control-3C23K 10 mg/kg q7d4 | 9.83 | 0.01 | * | 4.41 | 0.04 | * |
| | control-paclitaxel 15 mg/kg q7d4 | 0.03 | 0.86 | | 0.28 | 0.60 | |
| | control-3C23K 10 mg/kg q7d4 + paclitaxel 15 mg/kg q7d4 | 11.11 | 0.00 | * | 4.42 | 0.04 | * |
| | 3C23K 10 mg/kg q7d4-paclitaxel 15 mg/kg q7d4 | 8.53 | 0.01 | * | 8.70 | 0.00 | * |
| | 3C23K 10 mg/kg q7d4-3C23K 10 mg/kg q7d4 + paclitaxel 15 mg/kg q7d4 | 0.19 | 0.67 | | 0.10 | 0.75 | |
| | paclitaxel 15 mg/kg q7d4-C23K 10 mg/kg q7d4 + paclitaxel 15 mg/kg q7d4 | 9.71 | 0.01 | * | 9.30 | 0.00 | * |
| D27 | control-3C23K 10 mg/kg q7d4 | 8.21 | 0.01 | * | 4.87 | 0.03 | * |
| | control-paclitaxel 15 mg/kg q7d4 | 0.74 | 0.40 | | 1.10 | 0.29 | |
| | control-3C23K 10 mg/kg q7d4 + paclitaxel 15 mg/kg q7d4 | 11.09 | 0.00 | * | 6.90 | 0.01 | * |
| | 3C23K 10 mg/kg q7d4-paclitaxel 15 mg/kg q7d4 | 8.92 | 0.01 | * | 8.66 | 0.00 | * |
| | 3C23K 10 mg/kg q7d4-3C23K 10 mg/kg q7d4 + paclitaxel 15 mg/kg q7d4 | 1.75 | 0.21 | | 1.11 | 0.29 | |
| | paclitaxel 15 mg/kg q7d4-3C23K 10 mg/kg q7d4 + paclitaxel 15 mg/kg q7d4 | 14.22 | 0.00 | * | 10.61 | 0.00 | * |

TABLE 13-continued

Statistical analysis

| Day | Contrast between groups | ANOVA F-ratio | ANOVA P-value | Sig. | Kruskal - Wallis Test | Kruskal - Wallis P-value | Sig. |
|---|---|---|---|---|---|---|---|
| D31 | control-3C23K 10 mg/kg q7d4 | 10.00 | 0.01 | * | 4.86 | 0.03 | * |
|  | control-paclitaxel 15 mg/kg q7d4 | 0.61 | 0.45 |  | 0.89 | 0.34 |  |
|  | control-3C23K 10 mg/kg q7d4 + paclitaxel 15 mg/kg q7d4 | 12.60 | 0.00 | * | 6.67 | 0.01 | * |
|  | 3C23K 10 mg/kg q7d4-paclitaxel 15 mg/kg q7d4 | 8.01 | 0.01 | * | 8.66 | 0.00 | * |
|  | 3C23K 10 mg/kg q7d4-3C23K 10 mg/kg q7d4 + paclitaxel 15 mg/kg q7d4 | 1.44 | 0.25 |  | 1.75 | 0.19 |  |
|  | paclitaxel 15 mg/kg q7d4-3C23K 10 mg/kg q7d4 + paclitaxel 15 mg/kg q7d4 | 11.13 | 0.00 | * | 10.68 | 0.00 | * |
| D35 | control-3C23K 10 mg/kg q7d4 | 8.26 | 0.01 | * | 5.11 | 0.02 | * |
|  | control-paclitaxel 15 mg/kg q7d4 | 0.02 | 0.90 |  | 0.10 | 0.75 |  |
|  | control-3C23K 10 mg/kg q7d4 + paclitaxel 15 mg/kg q7d4 | 9.78 | 0.01 | * | 8.09 | 0.00 | * |
|  | 3C23K 10 mg/kg q7d4-paclitaxel 15 mg/kg q7d4 | 10.47 | 0.01 | * | 8.65 | 0.00 | * |
|  | 3C23K 10 mg/kg q7d4-3C23K 10 mg/kg q7d4 + paclitaxel 15 mg/kg q7d4 | 0.62 | 0.45 |  | 1.23 | 0.27 |  |
|  | paclitaxel 15 mg/kg q7d4-3C23K 10 mg/kg q7d4 + paclitaxel 15 mg/kg q7d4 | 12.39 | 0.00 | * | 9.33 | 0.00 | * |
| D41 | control-3C23K 10 mg/kg q7d4 | 11.82 | 0.00 | * | 5.36 | 0.02 | * |
|  | control-paclitaxel 15 mg/kg q7d4 | 0.06 | 0.81 |  | 0.20 | 0.65 |  |
|  | control-3C23K 10 mg/kg q7d4 + paclitaxel 15 mg/kg q7d4 | 15.82 | 0.00 | * | 7.14 | 0.01 | * |
|  | 3C23K 10 mg/kg q7d4-paclitaxel 15 mg/kg q7d4 | 12.64 | 0.00 | * | 7.71 | 0.01 | * |
|  | 3C23K 10 mg/kg q7d4-3C23K 10 mg/kg q7d4 + paclitaxel 15 mg/kg q7d4 | 1.63 | 0.22 |  | 1.75 | 0.19 |  |
|  | paclitaxel 15 mg/kg q7d4-3C23K 10 mg/kg q7d4 + paclitaxel 15 mg/kg q7d4 | 17.31 | 0.00 | * | 9.83 | 0.00 | * |
| D45 | 3C23K 10 mg/kg q7d4-3C23K 10 mg/kg q7d4 + paclitaxel 15 mg/kg q7d4 | 2.75 | 0.12 |  | 3.05 | 0.08 |  |
| D48 | 3C23K 10 mg/kg q7d4-3C23K 10 mg/kg q7d4 + paclitaxel 15 mg/kg q7d4 | 1.38 | 0.26 |  | 1.75 | 0.19 |  |
| D51 | 3C23K 10 mg/kg q7d4-3C23K 10 mg/kg q7d4 + paclitaxel 15 mg/kg q7d4 | 0.65 | 0.43 |  | 0.81 | 0.37 |  |

TABLE 14

Summary of the raw data for survival parameter

| Mouse number | Groups | Days | Observations |
|---|---|---|---|
| 1 | NaCl | 34 |  |
| 2 | NaCl | 41 |  |
| 3 | NaCl | 41 |  |
| 4 | NaCl | 45 |  |
| 5 | NaCl | 45 |  |
| 6 | NaCl | 45 |  |
| 7 | NaCl | 55 |  |
| 8 | NaCl | 55 |  |
| 1 | 3C23K 10 mg/kg q7d4 | 51 |  |
| 2 | 3C23K 10 mg/kg q7d4 | 55 |  |
| 3 | 3C23K 10 mg/kg q7d4 | 62 |  |
| 4 | 3C23K 10 mg/kg q7d4 | 69 |  |
| 5 | 3C23K 10 mg/kg q7d4 | 76 |  |
| 6 | 3C23K 10 mg/kg q7d4 | 83 | End of experiment TV 1615 mm3 |
| 7 | 3C23K 10 mg/kg q7d4 | 83 | End of experiment TV 1463 mm3 |
| 8 | 3C23K 10 mg/kg q7d4 | 83 | End of experiment no tumour |
| 1 | Paclitaxel 15 mg/kg q7d4 | 34 |  |
| 2 | Paclitaxel 15 mg/kg q7d4 | 41 |  |
| 3 | Paclitaxel 15 mg/kg q7d4 | 41 |  |
| 4 | Paclitaxel 15 mg/kg q7d4 | 45 |  |
| 5 | Paclitaxel 15 mg/kg q7d4 | 45 |  |
| 6 | Paclitaxel 15 mg/kg q7d4 | 51 |  |
| 7 | Paclitaxel 15 mg/kg q7d4 | 51 |  |
| 8 | Paclitaxel 15 mg/kg q7d4 | 55 |  |
| 1 | 3C23K 10 mg/kg q7d4 + Paclitaxel 15 mg/kg q7d4 | 51 |  |
| 2 | 3C23K 10 mg/kg q7d4 + Paclitaxel 15 mg/kg q7d4 | 62 |  |
| 3 | 3C23K 10 mg/kg q7d4 + Paclitaxel 15 mg/kg q7d4 | 66 |  |
| 4 | 3C23K 10 mg/kg q7d4 + Paclitaxel 15 mg/kg q7d4 | 66 |  |
| 5 | 3C23K 10 mg/kg q7d4 + Paclitaxel 15 mg/kg q7d4 | 80 |  |
| 6 | 3C23K 10 mg/kg q7d4 + Paclitaxel 15 mg/kg q7d4 | 83 | End of experiment TV 413 mm3 |
| 7 | 3C23K 10 mg/kg q7d4 + Paclitaxel 15 mg/kg q7d4 | 83 | End of experiment No tumour |
| 8 | 3C23K 10 mg/kg q7d4 + Paclitaxel 15 mg/kg q7d4 | 83 | End of experiment No tumour |

TABLE 15

Survival parameters

Survival parameter

| Group | Mean | Median | SD |
|---|---|---|---|
| Control | 45 | 45 | 5 |
| 3C23K 10 mg/kg q7dx4 | 70 | 73 | 11 |
| Paclitaxel 15 mg/kg q7d4 | 45 | 45 | 5 |
| 3C23K 10 mg/kg + Paclitaxel 15 mg/kg q7dx4 | 72 | 72 | 11 |

Survival parameter: logrank test

| | chi-squared | p-value | sign. |
|---|---|---|---|
| Control-3C23K 10 mg/kg q7d4 | 11.15 | 0.00 | * |
| Control-paclitaxel 15 mg/kg q7d4 | 0.04 | 0.84 | |
| Control-3C23K 10 mg/kg q7d4 + paclitaxel 15 mg/kg q7d4 | 12.87 | 0.00 | * |
| 3C23K 10 mg/kg q7d4-paclitaxel 15 mg/kg q7d4 | 12.36 | 0.00 | * |
| 3C23K 10 mg/kg q7d4-3C23K 10 mg/kg q7d4 + paclitaxel 15 mg/kg q7d4 | 0.17 | 0.68 | |
| paclitaxel 15 mg/kg q7d4-3C23K 10 mg/kg q7d4 + paclitaxel 15 mg/kg q7d4 | 13.61 | 0.00 | * |

The invention claimed is:

1. A pharmaceutical composition comprising:
as active ingredient:
an anticancer agent selected from the group consisting of carboplatin, paclitaxel, doxorubicin, pegylated liposomal doxorubicin, and mixtures thereof, and
a mutated humanized 12G4 monoclonal antibody binding the human anti-Müllerian hormone type II receptor (AMHR-II) comprising or constituted by:
a) a light chain comprising or constituted by:
a variable region the amino acid sequence of which is represented by SEQ ID NO: 7 or SEQ ID NO: 8, and
a constant region the amino acid sequence of which is represented by SEQ ID NO: 3
b) a heavy chain comprising or constituted by:
a variable region the amino acid sequence of which is represented by SEQ ID NO: 9 or SEQ ID NO: 10, and
a constant region the amino acid sequence of which is represented by SEQ ID NO: 6; and
a pharmaceutically acceptable vehicle.

2. The pharmaceutical composition according to claim 1, wherein said antibody possesses affinity for AMHR-II characterized by a $K_D$ of less than $10^{-7}$ M.

3. The pharmaceutical composition according to claim 2, wherein said antibody possesses affinity for AMHR-II characterized by a $K_D$ of less than $10^{-8}$ M.

4. The pharmaceutical composition according to claim 2, wherein said antibody possesses affinity for AMHR-II characterized by a $K_D$ in the range from $10^{-9}$ M to $10^{-11}$ M.

5. The pharmaceutical composition according to claim 1, wherein said antibody is produced by a 3C23K clone.

6. The pharmaceutical composition according to claim 5, comprising the mutated 12G4 monoclonal antibody produced by the 3C23K clone, and carboplatin.

7. The pharmaceutical composition according to claim 5, comprising the mutated 12G4 monoclonal antibody produced by the 3C23K clone, and paclitaxel.

8. The pharmaceutical composition according to claim 1, wherein said antibody is a recombinant antibody produced by animal transgenesis.

9. The pharmaceutical composition according to claim 1, in a formulation intended for administration by the intravenous or intraperitoneal route.

10. The pharmaceutical composition according to claim 1, wherein a therapeutically effective quantity of antibody administered to a patient is in a range from about 0.07 mg to about 35000 mg.

11. The pharmaceutical composition according to claim 10, wherein the therapeutically effective quantity of antibody administered to a patient is in a range from about 0.7 mg to about 7000 mg.

12. The pharmaceutical composition according to claim 10, wherein the therapeutically effective quantity of antibody administered to a patient is in a range from about 0.7 mg to about 1400 mg.

13. The pharmaceutical composition according to claim 10, wherein the therapeutically effective quantity of antibody administered to a patient is in a range from about 0.7 mg to about 700 mg.

14. The pharmaceutical composition according to claim 10, wherein the therapeutically effective quantity of antibody administered to a patient is in a range from about 0.7 mg to about 70 mg.

15. The pharmaceutical composition according to claim 1, wherein a therapeutically effective quantity of anticancer agent administered to a patient is in a range from about 10 mg to about 700 mg.

16. The pharmaceutical composition according to claim 15, wherein the therapeutically effective quantity of anticancer agent administered to a patient is in a range from about 20 mg to about 350 mg.

17. The pharmaceutical composition according to claim 15, wherein the therapeutically effective quantity of anticancer agent administered to a patient is about 110 mg.

18. The pharmaceutical composition according to claim 1, wherein a dose of antibody administered to a patient is about 70 mg and a dose of anticancer agent administered to the patient is about 110 mg.

19. The pharmaceutical composition according to claim 1, wherein a therapeutically effective quantity of antibody is from 0.1 mg/kg to 100 mg/kg.

20. Composition A method for preventing or treating a pathology associated with human anti-Müllerian hormone type II receptor (AMHR-II) comprising administering to a subject in need thereof a composition comprising:

an anticancer agent selected from the group consisting of carboplatin, paclitaxel, doxorubicin, pegylated liposomal doxorubicin, and mixtures thereof, and a mutated humanized 12G4 monoclonal antibody binding the human anti-Müllerian hormone type II receptor (AMHR-II)comprising or constituted by:
a) a light chain comprising or constituted by:
a variable region the amino acid sequence of which is represented by SEQ ID NO: 7 or SEQ ID NO: 8, and
a constant region the amino acid sequence of which is represented by SEQ ID NO: 3
b) a heavy chain comprising or constituted by:
a variable region the amino acid sequence of which is represented by SEQ ID NO: 9 or SEQ ID NO: 10, and
a constant region the amino acid sequence of which is represented by SEQ ID NO: 6.

21. The method according to claim 20, wherein the pathology associated with the human anti-Müllerian hormone type II receptor (AMHR-II) is cancer.

22. The method according to claim 21, wherein the cancer is an ovarian cancer.

23. The method according to claim 21, wherein the cancer is an endometrial cancer.

24. The method according to claim 21, wherein the cancer is a mixed Müllerian malignant tumor of the uterus.

* * * * *